US008343893B2

(12) United States Patent
Jeschke et al.

(10) Patent No.: US 8,343,893 B2
(45) Date of Patent: Jan. 1, 2013

(54) SUBSTITUTED ENAMINOCARBONYL COMPOUNDS

(75) Inventors: Peter Jeschke, Bergisch Gladbach (DE); Thomas Schenke, Bergisch Gladbach (DE); Robert Velten, Langenfeld (DE); Peter Lümmen, Idstein (DE); Olga Malsam, Rösrath (DE); Ulrich Görgens, Ratingen (DE); Arnd Voerste, Köln (DE)

(73) Assignee: Bayer Cropscience AG, Monheim (DE)

( * ) Notice: Subject to any disclaimer, the term of this patent is extended or adjusted under 35 U.S.C. 154(b) by 57 days.

(21) Appl. No.: 12/817,919

(22) Filed: Jun. 17, 2010

(65) Prior Publication Data

US 2010/0324103 A1   Dec. 23, 2010

(30) Foreign Application Priority Data

Jun. 18, 2009  (EP) .................................... 09163137

(51) Int. Cl.
*A01N 43/40* (2006.01)
*A61K 31/435* (2006.01)
*C07D 213/08* (2006.01)

(52) U.S. Cl. ......... 504/244; 514/277; 546/250; 546/255
(58) Field of Classification Search ................. 546/250, 546/255; 504/244, 250; 514/277
See application file for complete search history.

(56) References Cited

U.S. PATENT DOCUMENTS

| | | | |
|---|---|---|---|
| 4,030,994 | A | 6/1977 | Kollonitsch |
| 4,195,036 | A | 3/1980 | Gozzo et al. |
| 4,631,081 | A | 12/1986 | Watson et al. |
| 4,748,243 | A | 5/1988 | Beck et al. |
| 4,778,896 | A | 10/1988 | Gallenkamp |
| 4,990,622 | A | 2/1991 | Jelich |
| 5,116,993 | A | 5/1992 | Jelich |
| 5,175,301 | A | 12/1992 | Minamida et al. |
| 5,180,833 | A | 1/1993 | Uneme et al. |
| 5,346,343 | A | 9/1994 | Babel |
| 5,420,270 | A | 5/1995 | Chandrakumar et al. |
| 5,679,796 | A | 10/1997 | Kraatz |
| 5,811,555 | A | 9/1998 | Wakasugi et al. |
| 5,894,073 | A | 4/1999 | Matsuda et al. |
| 6,022,974 | A | 2/2000 | Werbitzky et al. |
| 6,187,927 | B1 | 2/2001 | Pitterna |
| 6,252,087 | B1 | 6/2001 | Koch et al. |
| 7,230,115 | B1 | 6/2007 | Dolbier et al. |
| 7,393,844 | B2 | 7/2008 | Goble et al. |
| 7,687,634 | B2 | 3/2010 | Loso et al. |
| 2003/0069242 | A1 | 4/2003 | Toriyabe et al. |
| 2007/0299264 | A1 | 12/2007 | Huang et al. |
| 2008/0305955 | A1 | 12/2008 | Bretschneider et al. |
| 2009/0247551 | A1 | 10/2009 | Jeschke et al. |
| 2009/0253749 | A1 | 10/2009 | Jeschke et al. |
| 2010/0048646 | A1 | 2/2010 | Jeschke et al. |
| 2010/0204480 | A1 | 8/2010 | Lui et al. |
| 2010/0240705 | A1 | 9/2010 | Jeschke et al. |
| 2011/0306499 | A1 | 12/2011 | Bretschneider et al. |

FOREIGN PATENT DOCUMENTS

| | | | |
|---|---|---|---|
| DE | 27 48 814 | A1 | 5/1978 |
| DE | 33 14 196 | A1 | 9/1983 |
| DE | 36 30 046 | A1 | 3/1988 |
| DE | 36 31 538 | A1 | 3/1988 |
| DE | 44 17 752 | A1 | 11/1995 |
| EP | 0 104 876 | A2 | 4/1984 |
| EP | 0 302 389 | A2 | 2/1989 |
| EP | 0 373 464 | A2 | 6/1990 |
| EP | 0 393 453 | A2 | 10/1990 |
| EP | 0 446 913 | A1 | 9/1991 |
| EP | 0 539 588 | A1 | 5/1993 |
| EP | 0 565 050 | A1 | 10/1993 |
| EP | 0 569 947 | A1 | 11/1993 |
| EP | 0 775 700 | A1 | 5/1997 |
| EP | 0 780 384 | A2 | 6/1997 |
| EP | 0 794 180 | A1 | 9/1997 |
| EP | 2 039 678 | A1 | 3/2009 |
| JP | 5-239034 | A | 9/1993 |
| WO | WO 97/10226 | A1 | 3/1997 |
| WO | WO 99/55668 | A1 | 11/1999 |
| WO | WO 01/07414 | A1 | 2/2001 |
| WO | WO 2004/082616 | A2 | 9/2004 |
| WO | WO 2006/089633 | A2 | 8/2006 |
| WO | WO 2007/095229 | A2 | 8/2007 |
| WO | WO 2007/115643 | A1 | 10/2007 |
| WO | WO 2007/115644 | A1 | 10/2007 |
| WO | WO 2007/115646 | A1 | 10/2007 |
| WO | WO 2007/149134 | A1 | 12/2007 |
| WO | WO 2008/009360 | A2 | 1/2008 |

(Continued)

OTHER PUBLICATIONS

Grimmett, M.R., and Keene B.R.T. In ., "Advances in Heterocyclic Chemistry," 43:148-161, A. R. Katritzky (Ed.), Academic Press, United States (1988).

Hiroi, K., and Kato, F., "Stereochemical studies of the palladium-catalyzed rearrangements of chiral 2-alkynyl sulfinates into chiral allenyl sulfones," *Tetrahedron* 57:1543-1550, Elsevier Science Ltd., England (2001).

Jung, C.-K, et al., "Phosphine-Mediated Reductive Condensation of γ-Acyloxy Butynoates: A Diversity Oriented Strategy for the Construction of Substituted Furans," *J. Am. Chem. Soc.* 126:4118-4119, American Chemical Society, United States (2004).

(Continued)

*Primary Examiner* — Paul V. Ward
(74) *Attorney, Agent, or Firm* — Sterne, Kessler, Goldstein & Fox P.L.L.C.

(57) ABSTRACT

The present application relates to substituted enaminocarbonyl compounds of the formula (I)

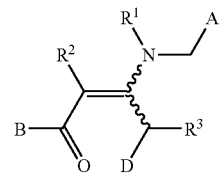

in which A, B, D, $R^1$ to $R^3$ are each as defined in the description, to processes for preparation thereof and to the use thereof for controlling animal pests.

18 Claims, No Drawings

FOREIGN PATENT DOCUMENTS

WO     WO 2008/067911 A1     6/2008

OTHER PUBLICATIONS

Kinugawa, M., et al., "Facile synthesis of the key intermediate of EO 9 via the formation of the indole skeleton using the Nenitzescu reaction," *J. Chem. Soc. Perkin Trans.* 1:2677-2678 Chemical Society of London, England (1995).

Kuneš, J., et al., "Synthesis and Antifungal Activity Evaluation of 3-Hetaryl-2,5-Dihydrofuran-2-Ones. An Unusual Fragmentation of the Oxazole Ring via 2,3-Selenoxide Shift, "*Collect. Czech. Chem. Commun.* 66:1809-1830, Institute of Organic Chemistry and Biochemistry, Czech Republic (2001).

Larock, R. C., and Liu, C.-L., "Mercury in Organic Chemistry. 24[1] Mercuration and Subsequent Carbonylation of 4-Hydroxy-2-alkyn-l-ones: A Novel Route to Furans, "*J. Org. Chem.* 48:2151-2158, American Chemical Sociezy, United States (1983).

Maezaki, N., et al., "Pd-catalyzed asymmetric sulfinylzincation of 1-alkynoates using 1-alkynyl sulfoxides bearing a chiral auxiliary," *Tetrahedron Asymmetry* 13:1961-1964, Elsevier Science Ltd., England (2002).

Nishiwaki, N., et al., "Synthesis of N-Modified 4-Aminopyridine-3-carboxylates by Ring Transformation," *Synlett* 9:1437-1439, Georg Thieme Verlag, Stuttgart, New York (2006).

Pesti, J. A., et al., "Efficient Pyridinylmethyl Functionalization: Synthesis of 10,10-Bis[(2-fluoro-4-pyridinyl)methyl]-9(10H)-anthracenone (DMP 543), an Acetylcholine Release Enhancing Agent," *J. Org. Chem.* 65:7718-7722, American Chemical Society, United States (2000).

Beholz, L. G., et al., "Formation of Dihydropyridone- and Pyridone-Based Peptide Analogs through Aza-Annulation of β-Enamino Ester and Amide Substrates with α-Amido Acrylate Derivatives," *J. Org. Chem.* 62:1033-1042, American Chemical Society, United States (1997).

Cabanal-Duvillard, I., and Berrien, J.-F., "A Simple Access to Key Pyridine Building Blocks," *Heterocyclic Communications* 5(3):257-262, De Gruyter, Germany (1999).

Cheeseman, G.W.H., and Wrstiuk, E.S.G., in "Advances in Heterocyclic Chemistry," A. R. Katritzky (Ed.) 22:390-392, Academic Press, United (1978).

Clasby, M. C., et al., "Himbacine derived thrombin receptor antagonists: Discovery of a new tricyclic core," *Bioorganic & Medicinal Chemistry Letters* (17):3647-3651, Elsevier Ltd., England (2007).

Comer, E., and Murphy, W.S., "The bromoquinone annulation reaction: a formal total synthesis of EO9," *Arkivoc* vii:286-296, Arkat USA, Inc, United States (2003).

Covarrubias-Zúñiga, A., et al., "Synthesis of Resorcinols Via a Michael Addition-Dieckman Cyclization Sequence of Dimethyl 1,3-Acetonedicarboxylate Anion With Alkyl Alkynoates," *Synthetic Communications* 28(18):3461-3469, Marcel Dekker, Inc., United States (1998).

David, O., et al., "New Access to Chiral Cycle ω-Oxygenated β-Enamino Esters by Intramolecular Aminocyclisation Reactions," *Heterocycles* 62:839-846, Elsevier B.V., Netherlands (2004).

Gassen, K.R., and Baasner, B., "Fluorinated Cyclopropanecarboxylic Acids and Their Derivatives," *Journal of Fluorine Chemistry* 49:127-139, Elsevier Sequoia, Netherlands (1990).

Gilchrist, T.L., "Comprehensive Organic Synthesis," S. V. Ley, (Ed.), 7:748-750, Pergamon Press, England (1992).

Grigg, R., and Savic, V., "Palladium catalysed synthesis of pyrroles from enamines," *Chem. Commun.* 31(35):873-874, The Royal Society of Chemistry, England (2000).

Pévet, I., et al., "[2,3]- Wittig Sigmatropic Rearrangement of γ-Allyloxy-β-Enaminoesters," *Synlett* 5:663-666, Georg Thieme Verlag Stuttgart, New York (2003).

Prabhakar, P., et al., "A Mild and Efficient Chemoselective Protection of Primary Alcohols as Pivaloyl Esters Using La(NO$_3$)$_3$·6H$_2$O as a Catalyst under Solvent-free Conditions," *Chemistry Letters* 36(6):732-733, The Chemical Society of Japan, Japan (2007).

Raminelli, C., et al., "Kinetic resolution of propargylic and allylic alcohols by *Candida antarctica* lipase (Novozyme 435)," *Tetrahedron: Asymmetry* 15:3117-3122, Elsevier Ltd., England (2004).

Takahashi, T., et al., "Cationic Polymerization Behavior of Alkoxyallenes,"*Macromolecules* 28:866-869, American Chemical Society, United States (1995).

Tayama, E., and Hashimoto, R., "A facile synthetic method of α-quaternary-β,γ-unsaturated aldehydes via the stereoselective 1,4-elimination and α-regioselective Ferrier reaction," *Tetrahedron Letters* 48:7950-7952, Elsevier Ltd., England (2007).

Tišler, M., and Stanovnik, B., in "Advances in Heterocyclic Chemistry," A. R. Katritzky (Ed.) 9:285-291, Academic Press, United States (1968).

Tišler, M., et al., "Pyridazines and their Benzo Derivatives," *in Comprehensive Heterocyclic Chemistry* 3(2B):18-20, Academic Press, United States (1984).

Van Der Eycken, E., et al., "Synthesis of (E)-5-(2-arylvinyl)-2-(hetero)arlpyridines, (E)-2-(2-arylvinyl)-5-methoxycarbonylpyridines and (E,E)-2,5-bis(2-arylvinyl)pyridines as polarity and pH probes," *J. Chem. Soc., Perkin Trans.* 2:928-937, The Society of Chemistry, England (2002).

Yamamoto, Y., et al., "Synthesis of arylboronates via Cp*RuCl-catalyzed cycloaddition of alkynylboronates," *Tetrahedron* 62:4294-4305, Elsevier Ltd., England (2006).

English language Abstract of German Patent Publication No. DE 3 314 196 A1, European Patent Office, espacenet database—Worldwide (2001).

English language Abstract of German Patent Publication No. DE 4 417 752 A1, European Patent Office, espacenet database—Worldwide (2001).

English language Abstract of Japanese Patent Publication No. 5-239034 A, Japanese Patent Office, Patent & Utility Model Gazette DB, Patent Abstracts of Japan (1993).

International Search Report for International Application No. PCT/EP2010/003395, European Patent Office, Netherlands, mailed on Sep. 30, 2010.

SUBSTITUTED ENAMINOCARBONYL COMPOUNDS

The present application relates to substituted enaminocarbonyl compounds, to processes for preparation thereof and to the use thereof for controlling animal pests, especially those which damage plants, in particular arthropods, especially insects.

Substituted enaminocarbonyl compounds, for example γ-allyloxy-β-enamino esters are known (cf. I. Pevet et al., *Synlett* 5, 663-666, 2003), and some are used as intermediates for the synthesis of different heterocycles, for example of 3,4,5-trifunctionalized pyridines, N-methyldioxoindoles, indole-3-carboxylic acid derivatives or pyrroles (cf. γ-methoxy-β-enamino methyl esters: N. Nishiwaki et al., *Synlett* 9, 1437-1439, 2006; E. Comer, W. S. Murphy, ARKIVOC (Gainesville, Fla., USA) 7, 286-296, 2003; M. Kinugawa et al., *J. Chem. Soc., Perkin Trans.* 1: *Org. and Bio-Organic Chem.* 21, 2677-2678, 1995; EP 565 050 A1; γ-methoxy-β-enamino methyl esters with β-vinyl bromide functionality: R. Grigg, V. Savic *Chem. Commun.* (*Cambridge*) 10, 873-874, 2000).

EP-A1-2039678 describes a process for preparing 4-aminobut-2-enolides, in which specific substituted enaminocarbonyl compounds are used as intermediates.

WO2007/115643 describes cyclic enaminocarbonyl compounds, which are proposed for control of pests.

Modern crop protection compositions have to meet many requirements, for example in relation to level, duration and range of their action and possible use. Questions of toxicity play a role, as does the question of application rate and that of economic viability. The search for new crop protection compositions can therefore never be considered to be complete, and there is a constant need for new compounds with improved properties.

It is an object of the present invention to provide compounds which take account of the abovementioned aspects.

It has now been found that, surprisingly, particular substituted enaminocarbonyl compounds and the N-oxides and salts thereof are especially suitable for controlling animal pests and can therefore be used particularly efficiently in the agrochemical sector and in the animal health sector.

These enaminocarbonyl compounds are characterized by the formula (I)

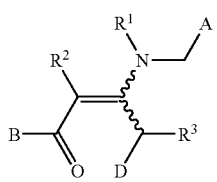

in which
A is an optionally substituted heterocycle;
B is a Z—$R^4$ radical in which
Z is oxygen, sulphur or optionally substituted nitrogen, and $R^4$ is hydrogen, $C_1$-$C_6$-alkyl, $C_1$-$C_6$-alkoxy-$C_1$-$C_6$-alkyl, $C_1$-$C_6$-alkylthio-$C_1$-$C_6$-alkyl, halo-$C_1$-$C_6$-alkyl, cyano-$C_1$-$C_6$-alkyl, $C_2$-$C_6$-alkenyl, $C_2$-$C_6$-alkynyl, $C_3$-$C_6$-cycloalkyl, $C_4$-$C_{10}$-dicycloalkyl, tri-$C_1$-$C_6$-alkylsilyl, tri-$C_1$-$C_6$-alkylsilyl-$C_1$-$C_6$-alkyl, hetaryl, hetaryl-$C_1$-$C_6$-alkyl, optionally substituted aryl, aryl-$C_1$-$C_6$-alkyl or aryl-$C_1$-$C_6$-alkoxy-$C_1$-$C_6$-alkyl;

D is a T-$R^5$ radical in which
T is oxygen, sulphur or optionally substituted nitrogen, and $R^5$ is hydrogen, formyl, $C_1$-$C_6$-alkyl, $C_1$-$C_6$-alkoxy-$C_1$-$C_6$-alkyl, halo-$C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_6$-alkylthio-$C_1$-$C_6$-alkyl, $C_2$-$C_6$-alkenyl, $C_3$-$C_6$-cycloalkyl, $C_2$-$C_6$-alkynyl, $C_1$-$C_6$-alkoxycarbonyl, $C_3$-$C_6$-cycloalkyloxycarbonyl, aryl, hetaryl, heterocyclyl, $C_1$-$C_6$-alkylcarbonyl, aryl-$C_1$-$C_6$-alkyl, hetaryl-$C_1$-$C_6$-alkyl, halo-$C_1$-$C_6$-alkylcarbonyl, arylcarbonyl, $C_1$-$C_6$-alkylsulphonyl, halo-$C_1$-$C_6$-alkylsulphonyl, aryl-$C_1$-$C_6$-aryloxy-$C_1$-$C_6$-alkyl, arylsulphonyl or tri-$C_1$-$C_6$-alkylsilyl, where the groups are optionally substituted;
$R^1$ is hydrogen, $C_1$-$C_6$-alkyl, $C_2$-$C_6$-alkenyl, $C_1$-$C_6$-alkynyl, $C_3$-$C_6$-cycloalkyl, $C_3$-$C_6$-cycloalkyl-$C_1$-$C_6$-alkyl, halo-$C_1$-$C_6$-alkyl, halo-$C_2$-$C_6$-alkenyl, halo-$C_3$-$C_6$-cycloalkyl, halo-$C_3$-$C_6$-cycloalkyl-$C_1$-$C_6$-alkyl, $C_1$-$C_6$-alkoxy or aryl-$C_1$-$C_6$-alkyl;
$R^2$ is hydrogen or halogen; and
$R^3$ is hydrogen or $C_1$-$C_6$-alkyl.

In a first embodiment, the invention relates to enaminocarbonyl compounds of the formula (I) in which
A is a heterocycle of the following formula

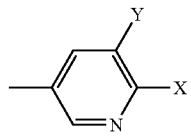

in which
X is halogen (preferably fluorine, chlorine or bromine), $C_1$-$C_6$-alkyl or halo-$C_1$-$C_6$-alkyl, preferably $CH_2F$, $CHF_2$, $CF_3$, $CH_2CF_3$, $CH_2CH_2F$, $CH_2CHF_2$ and
Y is halogen (preferably fluorine, chlorine or bromine), $C_1$-$C_6$-alkyl, halo-$C_1$-$C_6$-alkyl, preferably $CH_2F$, $CHF_2$, $CF_3$, $CH_2CF_3$, $CH_2CH_2F$, $CH_2CHF_2$, halo-$C_1$-$C_6$-alkoxy, preferably $OCH_2F$, $OCHF_2$, $OCF_3$, $OCH_2CF_3$, $OCH_2CH_2F$, $OCH_2CHF_2$, azido or cyano;
A is preferably one of the following heterocycles: 5,6-dibromopyrid-3-yl, 6-bromo-5-chloropyrid-3-yl, 6-bromo-5-fluoropyrid-3-yl, 5-chloro-6-iodopyrid-3-yl, 5,6-dichloropyrid-3-yl, 6-chloro-5-fluoropyrid-3-yl, 5-bromo-6-chloropyrid-3-yl, 6-chloro-5-methylpyrid-3-yl, 6-chloro-5-difluoromethylpyrid-3-yl, 6-chloro-1,4-pyridazin-3-yl, 2-chloropyrimid-5-yl and 2-chloro-1,3-thiazol-5-yl.

In a second embodiment, the invention relates to enaminocarbonyl compounds of the formula (I) in which
A is pyrid-2-yl; pyrid-4-yl; or pyrid-3-yl which is optionally 6-substituted by fluorine, chlorine, bromine, iodine, methyl, difluoromethyl, trifluoromethyl or trifluoromethoxy; pyridazin-3-yl which is optionally 6-substituted by chlorine or methyl; pyrazin-3-yl; 2-chloropyrazin-5-yl; 1,3-thiazol-5-yl which is optionally 2-substituted by chlorine or methyl; tetrahydrofuryl; pyrimidinyl; pyrazolyl; thiophenyl; oxazolyl; isoxazolyl; 1,2,4-oxadiazolyl; isothiazolyl; 1,2,4-triazolyl; 1,2,5-thiadiazolyl which is optionally substituted by fluorine, chlorine, bromine, cyano, nitro, or is substituted by in each case optionally fluoro- and/or chlorine-substituted $C_1$-$C_4$-alkyl, $C_1$-$C_3$-alkylthio, or $C_1$-$C_3$-alkylsulphonyl, preferably pyrid-3-yl which is 6-substituted by fluorine, chlorine, bromine, methyl or trifluoromethyl or trifluoromethoxy, i.e. 6-fluoropyrid-3-yl, 6-chloropyrid-3-yl, 6-bromopyrid-3-yl and 6-trifluoromethylpyrid-3-yl, 6-methylpyrid-3-yl, 6-trifluoromethoxypyrid-3-yl, or 2-methyl-1,3-thiazol-5-yl, 2-chloro-1,3-thiazol-5-yl, 2-chloro-1,3-thiazol-5-yl, 2-chloropyrazin-5-yl, 6-chloro-1,4-pyridazin-3-yl, 6-methyl-1,4-pyridazin-3-yl, A is preferably 6-fluoropyrid-3-yl, 6-chloropyrid-3-yl, 6-bromopyrid-3-yl, 6-chloro-1,4-pyridazin-3-yl or 2-chloro-1,3-thiazol-5-yl.

In a third embodiment, the invention relates to enaminocarbonyl compounds of the formula (I) in which A is as defined in the first or second embodiment and in which B is a Z—$R^4$ radical in which Z is oxygen or sulphur, preferably oxygen, and $R^4$ is hydrogen, $C_1$-$C_6$-alkyl, $C_1$-$C_4$-alkoxy-$C_1$-$C_6$-alkyl, $C_1$-$C_4$-alkylthio-$C_1$-$C_6$-alkyl, halo-$C_1$-$C_6$-alkyl, cyano-$C_1$-$C_4$-alkyl, $C_2$-$C_6$-alkenyl, $C_2$-$C_6$-alkynyl, $C_3$-$C_6$-cycloalkyl, di-$C_3$-$C_6$-cycloalkyl-$C_1$-$C_2$-alkyl, tri-$C_1$-$C_6$-alkylsilyl, tri-$C_1$-$C_6$-alkylsilyl-$C_1$-$C_2$-alkyl, hetaryl, hetaryl-$C_1$-$C_2$-alkyl, aryl-$C_1$-$C_2$-alkyl, aryl-$C_1$-$C_2$-alkyloxy-$C_1$-$C_3$-alkyl, phenyl or a nitro-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted phenyl, preferably hydrogen, methyl, ethyl, n-propyl, iso-propyl, n-butyl, iso-butyl, sec-butyl, tent-butyl, methoxyethyl, methylthioethyl, 2-methylthioethyl, 2,2,2-trichloroethyl, 2-chloroethyl, 2-bromoethyl, 2-iodoethyl, 2-cyanoethyl, allyl, methallyl, 3-buten-1-yl, propargyl, cyclopentyl, cyclohexyl, dicyclopropylmethyl, trimethylsilyl, di-tert-butylmethylsilyl, iso-propyldimethylsilyl, trimethylsilylmethyl, 2-(2'-pyridyl)ethyl, 4-picolyl, benzyl, 4-methoxybenzyl, 2,4-dimethoxybenzyl, 4-bromobenzyl, 4-methylsulphinylbenzyl, 4-nitrobenzyl, benzyloxymethyl, 4-methylthiophenyl, 4-nitro-phenyl or 2,3,4,5,6-pentafluorophenyl, more preferably hydrogen, methyl, ethyl or iso-propyl;

D is a T-$R^5$ radical in which

T is oxygen, sulphur or optionally substituted nitrogen, preferably oxygen, and $R^5$ is hydrogen, formyl, $C_1$-$C_6$-alkyl, $C_1$-$C_4$-alkoxy-$C_1$-$C_6$-alkyl, halo-$C_1$-$C_4$-alkoxy-$C_1$-$C_6$-alkyl, $C_1$-$C_4$-alkoxy-$C_1$-$C_4$-alkoxy-$C_1$-$C_6$-alkyl, $C_1$-$C_4$-alkylthio-$C_1$-$C_6$-alkyl, $C_2$-$C_6$-alkenyl, $C_3$-$C_6$-cycloalkyl, $C_2$-$C_6$-alkynyl, $C_1$-$C_6$-alkoxycarbonyl, $C_3$-$C_6$-cycloalkyloxycarbonyl, optionally substituted aryl, tetrahydropyran-2-yl, 3-bromotetrahydropyran-2-yl, tetrahydrothiopyran-2-yl, 1,4-dioxan-2-yl, tetrahydrofuranyl, $C_1$-$C_6$-alkylcarbonyl, optionally substituted aryl-$C_1$-$C_2$-alkyl, hetaryl-$C_1$-$C_2$-alkyl, halo-$C_1$-$C_6$-alkylcarbonyl, optionally substituted arylcarbonyl, $C_1$-$C_6$-alkylsulphonyl, halo-$C_1$-$C_6$-alkylsulphonyl, optionally substituted aryl-$C_1$-$C_4$-alkyloxy-$C_1$-$C_4$-alkyl, optionally substituted aryloxy-$C_1$-$C_4$-alkyl, optionally substituted arylsulphonyl or tri-$C_1$-$C_6$-alkylsilyl; preferably hydrogen, formyl, methyl, ethyl, n-propyl, iso-propyl, n-butyl, iso-butyl, sec-butyl, tert-butyl, allyl, methoxymethyl, 1-ethoxyethyl, tert-butoxymethyl, methylthiomethyl, methoxyethoxymethyl, 1-(2-chloroethoxy)ethyl, 1-methyl-1-methoxyethyl, cyclopropyl, cyclobutyl, propargyl, methoxycarbonyl, ethoxycarbonyl, cyclopropyloxycarbonyl, phenyl, tetrahydropyran-2-yl, methylcarbonyl, ethylcarbonyl, n-propylcarbonyl, iso-propylcarbonyl, tert-butylcarbonyl, trifluoromethylcarbonyl, 4-nitrophenylcarbonyl, 2,4-dinitrophenyl, 4-nitrophenyl, benzyl, 4-methoxybenzyl, 2,4-dimethoxybenzyl, 3,4-dimethoxybenzyl, 4-nitrobenzyl, 2,6-dichlorobenzyl, 4-methoxybenzyloxymethyl, 4-nitrobenzyloxymethyl, 2-picolyl, 4-picolyl, methylsulphonyl, ethylsulphonyl, 4-methoxyphenyl, trifluoromethylsulphonyl, para-toluenesulphonyl, trimethylsilyl, triethylsilyl, triisopropylsilyl, dimethylisopropylsilyl or tert-butyldimethylsilyl; more preferably methylcarbonyl, ethylcarbonyl, tert-butylcarbonyl or methoxycarbonyl;

$R^1$ is hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl, $C_1$-$C_6$-alkoxy, aryl-$C_1$-$C_4$-alkyl or fluoro-substituted $C_1$-$C_6$-alkyl, $C_2$-$C_6$-alkenyl, $C_3$-$C_6$-cycloalkyl or $C_3$-$C_6$-cycloalkyl-$C_1$-$C_4$-alkyl, preferably methyl, ethyl, allyl, propargyl, 2-fluoroethyl, 2,2-difluoroethyl, cyclopropyl, 2-fluorocyclopropyl or methoxy, more preferably methyl, cyclopropyl or 2,2-difluoroethyl;

$R^2$ is hydrogen, fluorine or chlorine; and $R^3$ is hydrogen or $C_1$-$C_6$-alkyl.

The invention further comprises a process for preparing the inventive compounds, comprising the following reaction steps (a) reacting a compound of the formula (II)

(II)

with a compound of the formula (III)

(III)

in which

B, D and $R^3$ are each as defined here and LG is a suitable leaving group, especially halo-$C_1$-$C_8$-alkoxy, $C_1$-$C_8$-alkanoyloxy, mercapto, $C_1$-$C_8$-alkylthio, halo-$C_1$-$C_8$-alkylthio or halogen; LG is preferably $C_1$-$C_8$-alkoxy, especially methoxy, ethoxy or iso-propoxy, preferably in the presence of a basic auxiliary and of a diluent, to give a compound of the formula (IV); and (b) reacting a compound of the formula (IV)

(IV)

with a compound of the formula (V)

$HN(R^1)$—$CH_2$-A  (V)

in which B, D, A and $R^1$ and $R^3$ are each as defined here, preferably in the presence of a diluent.

The invention further comprises a composition for controlling animal pests, preferably arthropods, especially insects, which includes at least one inventive compound in an insecticidally effective amount.

The invention further comprises the use of an inventive compound for controlling animal pests in the agrochemical sector (plant pests) and/or in the animal health sector, and to a method for controlling animal pests, characterized in that an inventive compound or an inventive composition is allowed to act on the pests and/or their habitat.

The inventive compounds may, depending on the type of substituents, be present as geometric and/or as optically active isomers or corresponding isomer mixtures in different compositions. These stereoisomers are, for example, enantiomers, diastereomers, atropisomers or geometric isomers. The invention thus comprises pure stereoisomers and any desired mixtures of these isomers.

In the general formula (I) and all other formulae in the present invention, the alkyl, alkoxy, haloalkyl, haloalkoxy, alkylamino, alkylsulphinyl and alkylsulphonyl radicals, and the corresponding unsaturated and/or substituted radicals in the carbon skeleton, may each be straight-chain or branched and substituted or unsubstituted. Unless stated specifically, the lower carbon skeletons are preferred for these radicals, for example having 1 to 6 carbon atoms, especially 1 to 4 carbon atoms, or in the case of unsaturated groups having 2 to 6 carbon atoms, especially 2 to 4 carbon atoms.

Alkyl radicals, including in the combined definitions such as alkoxy, haloalkyl, etc., are, for example, methyl; ethyl; propyl such as n- or iso-propyl; butyl such as n-, iso-, tert- or 2-butyl; pentyl such as n-pentyl, iso-pentyl and neo-pentyl; hexyl such as n-hexyl, iso-hexyl, 3-methylpentyl, 2,2-dimethylbutyl and 2,3-dimethylbutyl; and heptyl such as n-heptyl, 1-methylhexyl and 1,4-dimethylpentyl.

Alkenyl and alkynyl radicals are defined as the possible unsaturated radicals corresponding to the alkyl radicals; where at least one double bond or triple bond, preferably one double bond or triple bond, is present. Alkenyl is, for example, vinyl, 1-allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, ethynyl, propargyl/propynyl, but-2-yn-1-yl, but-3-yn-1-yl and 1-methylbut-3-yn-1-yl. They may be substituted or unsubstituted.

Cycloalkyl groups are, for example, cyclopropyl, cyclobutyl, cyclopentyl, cyclohexyl, cycloheptyl and cyclooctyl. The cycloalkyl groups may occur in bi- or tricyclic form. They may be substituted or unsubstituted.

When haloalkyl groups and haloalkyl radicals of haloalkoxy, haloalkenyl, haloalkynyl inter alia are specified, the lower carbon skeletons are preferred for these radicals, for example having 1 to 6 carbon atoms or 2 to 6, especially 1 to 4 carbon atoms or preferably 2 to 4 carbon atoms, as are the corresponding unsaturated and/or substituted radicals, each in straight-chain or branched form in the carbon skeleton, and substituted or unsubstituted. Examples are trifluoromethyl, difluoromethyl, 2,2,2-trifluoroethyl, trifluoroallyl and 1-chloroprop-1-yl-3-yl.

Halogen is fluorine, chlorine, bromine or iodine.

Haloalkyl, -alkenyl, -alkynyl, -cycloalkyl, -alkylsulphonyl and -alkylcarbonyl mean alkyl, alkenyl, alkynyl, cycloalkyl, alkylsulphonyl and alkylcarbonyl partly or fully substituted by halogen, preferably by fluorine, chlorine or bromine, especially by fluorine and/or chlorine, e.g. monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same applies to haloalkenyl, -alkynyl, -cycloalkyl, -alkylsulphonyl and -alkylcarbonyl, and other halogen-substituted radicals.

Aryl is a mono-, bi- or polycyclic aromatic system, for example phenyl or naphthyl, preferably phenyl. Aryl may be substituted or unsubstituted.

A heterocyclic radical (=heterocyclyl) contains at least one heterocyclic ring (=carbocyclic ring in which at least one carbon atom is replaced by a heteroatom, preferably by a heteroatom from the group consisting of N, O, S, P, B, Si, Se), which is saturated, unsaturated or heteroaromatic and may be unsubstituted or substituted, where the bonding site is localized on one ring atom. Unless defined differently, the heterocyclic ring preferably contains 3 to 9 ring atoms, especially 3 to 6 ring atoms, and one or more, preferably 1 to 4, especially 1, 2 or 3, heteroatoms in the heterocyclic ring, preferably from the group consisting of N, O, and S, although two oxygen atoms should not be directly adjacent. Examples of heterocyclyl groups are tetrahydropyran-2-yl, tetrahydrothiopyran-2-yl, 1,4-dioxan-2-yl and tetrahydrofuranyl.

The term heteroaryl or hetaryl is understood in the context of the present invention to mean systems as defined above under "heterocyclyl", but which are heteroaromatic, i.e. are a fully unsaturated aromatic heterocyclic compound and are substituted or unsubstituted.

Unless defined differently, "substituted" in the context of the present invention means that the corresponding group may be substituted by one or more substituents, and independently by one or more identical or different substituents.

Substituted radicals, such as a substituted alkyl, alkenyl, alkynyl, cycloalkyl, cycloalkenyl, aryl, phenyl, benzyl, heterocyclyl and hetoaryl radical, are, for example a substituted radical derived from the unsubstituted base skeleton, where the substituents are, for example, one or more, preferably 1, 2 or 3, radicals from the group of halogen, alkoxy, alkylthio, hydroxyl, amino, nitro, carboxyl or a group equivalent to the carboxyl group, cyano, isocyano, azido, alkoxycarbonyl, alkylcarbonyl, formyl, carbamoyl, mono- and dialkylaminocarbonyl, substituted amino, such as acylamino, mono- and dialkylamino, trialkylsilyl and optionally substituted cycloalkyl, optionally substituted aryl, optionally substituted heterocyclyl, where each of the latter cyclic groups may also be bonded via heteroatoms or divalent functional groups as for the alkyl radicals mentioned, and alkylsulphinyl, including both enantiomers of the alkylsulphonyl group, alkylsulphonyl, alkylphosphinyl, alkylphosphonyl and, in the case of cyclic radicals (="cyclic base skeleton"), also alkyl, haloalkyl, alkylthioalkyl, alkoxyalkyl, optionally substituted mono- and dialkylaminoalkyl and hydroxyalkyl; the term "substituted radicals", such as substituted alkyl, etc., includes, as substituents, in addition to the saturated hydrocarbonaceous radicals mentioned, corresponding unsaturated aliphatic and aromatic radicals, such as optionally substituted alkenyl, alkynyl, alkenyloxy, alkynyloxy, alkenylthio, alkynylthio, alkenyloxycarbonyl, alkynyloxycarbonyl, alkenylcarbonyl, alkynylcarbonyl, mono- and dialkenylaminocarbonyl, mono- and dialkynylaminocarbonyl, mono- and dialkenylamino, mono- and dialkynylamino, trialkenylsilyl, trialkynylsilyl, optionally substituted cycloalkenyl, optionally substituted cycloalkynyl, phenyl, phenoxy, etc. In the case of substituted cyclic radicals with aliphatic moieties in the ring, cyclic systems with those substituents bonded to the ring by a double bond, for example by an alkylidene group such as methylidene or ethylidene or an oxo group, imino group or substituted imino group, are also included.

The substituents mentioned by way of example ("first substituent level") can, when they contain hydrocarbonaceous moieties, optionally be further substituted there ("second substituent level"), for example by one of the substituents as defined for the first substituent level. Corresponding further substituent levels are possible. The term "substituted radical" preferably encompasses only one or two substituent levels.

Preferred substituents for the substituent levels are, for example, amino, hydroxyl, halogen, nitro, cyano, isocyano, mercapto, isothiocyanato, carboxyl, carboxamide, $SF_5$, aminosulphonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulphenyl, alkylsulphinyl, including both enantiomers of the alkylsulphinyl group, alkylsulphonyl, monoalkylaminosulphonyl, dialkylaminosulphonyl, alkylphosphinyl, alkylphosphonyl, including both enantiomers for alkylphosphinyl and alkylphosphonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino, benzylamino, heterocyclyl and trialkylsilyl.

As already mentioned, preferred radicals having carbon atoms are those having 1 to 6 carbon atoms, preferably 1 to 4 carbon atoms, especially 1 or 2 carbon atoms. Preference is generally given to substituents from the group of halogen, e.g. fluorine, chlorine and bromine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano.

Optionally substituted aryl or heteroaryl is preferably phenyl or heteroaryl, which is unsubstituted or mono- or polysubstituted, preferably up to trisubstituted, by identical or different radicals from the group of halogen, $(C_1-C_4)$-alkyl, $(C_3-C_6)$-cycloalkyl, $(C_1-C_4)$-alkoxy, $(C_1-C_4)$-haloalkyl, $(C_1-C_4)$-haloalkoxy, $(C_1-C_4)$-alkylthio, cyano and nitro, e.g. ortho-, meta- and para-tolyl, dimethylphenyls, 2-, 3- and 4-chlorophenyl, 2-, 3- and 4-trifluoromethyl and 2-, 3- and 4-trichlormethylphenyl, 2,4-, 3,5-, 2,5- and 2,3-dichlorophenyl, ortho-, meta- and para-methoxyphenyl.

In one emphasized group of compounds of the formula (I), $R^3$ is hydrogen, B is iso-propoxy and A is 6-chloropyrid-3-yl.

In a further emphasized group of compounds of the formula (I), $R^3$ is hydrogen, B is iso-propoxy and A is 6-bromopyrid-3-yl.

In a further emphasized group of compounds of the formula (I), $R^3$ is hydrogen, B is iso-propoxy and A is 6-fluoropyrid-3-yl.

In a further emphasized group of compounds of the formula (I), $R^3$ is hydrogen, B is iso-propoxy and A is 6-trifluoromethylpyrid-3-yl.

In a further emphasized group of compounds of the formula (I), $R^3$ is hydrogen, B is iso-propoxy and A is 2-chloro-1,3-thiazol-5-yl.

In a further emphasized group of compounds of the formula (I), $R^3$ is hydrogen, B is iso-propoxy and A is 5,6-dibromopyrid-3-yl.

In a further emphasized group of compounds of the formula (I), $R^3$ is hydrogen, B is iso-propoxy and A is 6-bromo-5-chloropyrid-3-yl.

In a further emphasized group of compounds of the formula (I), $R^3$ is hydrogen, B is iso-propoxy and A is 6-bromo-5-fluoropyrid-3-yl.

In a further emphasized group of compounds of the formula (I), $R^3$ is hydrogen, B is iso-propoxy and A is 5-chloro-6-iodopyrid-3-yl.

In a further emphasized group of compounds of the formula (I), $R^3$ is hydrogen, B is iso-propoxy and A is 5,6-dichloropyrid-3-yl.

In a further emphasized group of compounds of the formula (I), $R^3$ is hydrogen, B is iso-propoxy and A is 6-chloro-5-fluoropyrid-3-yl.

In a further emphasized group of compounds of the formula (I), $R^3$ is hydrogen, B is iso-propoxy and A is 5-bromo-6-chloropyrid-3-yl.

In a further emphasized group of compounds of the formula (I), $R^3$ is hydrogen, B is iso-propoxy and A is 6-chloro-5-methylpyrid-3-yl.

In a further emphasized group of compounds of the formula (I), $R^3$ is hydrogen, B is iso-propoxy and A is 6-chloro-5-difluoromethylpyrid-3-yl.

In a further emphasized group of compounds of the formula (I), $R^2$ and $R^3$ are each hydrogen, B is iso-propoxy and A is 6-chloropyrid-3-yl.

In a further emphasized group of compounds of the formula (I), $R^2$ and $R^3$ are each hydrogen, B is iso-propoxy and A is 6-bromopyrid-3-yl.

In a further emphasized group of compounds of the formula (I), $R^2$ and $R^3$ are each hydrogen, B is iso-propoxy and A is 6-fluoropyrid-3-yl.

In a further emphasized group of compounds of the formula (I), $R^2$ and $R^3$ are each hydrogen, B is iso-propoxy and A is 6-trifluoromethylpyrid-3-yl.

In a further emphasized group of compounds of the formula (I), $R^2$ and $R^3$ are each hydrogen, B is iso-propoxy and A is 2-chloro-1,3-thiazol-5-yl.

In a further emphasized group of compounds of the formula (I), $R^2$ and $R^3$ are each hydrogen, B is iso-propoxy and A is 5,6-dibromopyrid-3-yl.

In a further emphasized group of compounds of the formula (I), $R^2$ and $R^3$ are each hydrogen, B is iso-propoxy and A is 6-bromo-5-chloropyrid-3-yl.

In a further emphasized group of compounds of the formula (I), $R^2$ and $R^3$ are each hydrogen, B is iso-propoxy and A is 6-bromo-5-fluoropyrid-3-yl.

In a further emphasized group of compounds of the formula (I), $R^2$ and $R^3$ are each hydrogen, B is iso-propoxy and A is 5-chloro-6-iodopyrid-3-yl.

In a further emphasized group of compounds of the formula (I), $R^2$ and $R^3$ are each hydrogen, B is iso-propoxy and A is 5,6-dichloropyrid-3-yl.

In a further emphasized group of compounds of the formula (I), $R^2$ and $R^3$ are each hydrogen, B is iso-propoxy and A is 6-chloro-5-fluoropyrid-3-yl.

In a further emphasized group of compounds of the formula (I), $R^2$ and $R^3$ are each hydrogen, B is iso-propoxy and A is 5-bromo-6-chloropyrid-3-yl.

In a further emphasized group of compounds of the formula (I), $R^2$ and $R^3$ are each hydrogen, B is iso-propoxy and A is 6-chloro-5-methylpyrid-3-yl.

In a further emphasized group of compounds of the formula (I), $R^2$ and $R^3$ are each hydrogen, B is iso-propoxy and A is 6-chloro-5-difluoromethylpyrid-3-yl.

In a further emphasized group of compounds of the formula (I), $R^2$ and $R^3$ are each hydrogen, B is methoxy and A is 6-chloropyrid-3-yl.

In a further emphasized group of compounds of the formula (I), $R^2$ and $R^3$ are each hydrogen, B is methoxy and A is 6-bromopyrid-3-yl.

In a further emphasized group of compounds of the formula (I), $R^2$ and $R^3$ are each hydrogen, B is methoxy and A is 6-fluoropyrid-3-yl.

In a further emphasized group of compounds of the formula (I), $R^2$ and $R^3$ are each hydrogen, B is methoxy and A is 6-trifluoromethylpyrid-3-yl.

In a further emphasized group of compounds of the formula (I), $R^2$ and $R^3$ are each hydrogen, B is methoxy and A is 2-chloro-1,3-thiazol-5-yl.

In a further emphasized group of compounds of the formula (I), $R^2$ and $R^3$ are each hydrogen, B is methoxy and A is 5,6-dibromopyrid-3-yl.

In a further emphasized group of compounds of the formula (I), $R^2$ and $R^3$ are each hydrogen, B is methoxy and A is 6-bromo-5-chloropyrid-3-yl.

In a further emphasized group of compounds of the formula (I), $R^2$ and $R^3$ are each hydrogen, B is methoxy and A is 6-bromo-5-fluoropyrid-3-yl.

In a further emphasized group of compounds of the formula (I), $R^2$ and $R^3$ are each hydrogen, B is methoxy and A is 5-chloro-6-iodopyrid-3-yl.

In a further emphasized group of compounds of the formula (I), $R^2$ and $R^3$ are each hydrogen, B is methoxy and A is 5,6-dichloropyrid-3-yl.

In a further emphasized group of compounds of the formula (I), $R^2$ and $R^3$ are each hydrogen, B is methoxy and A is 6-chloro-5-fluoropyrid-3-yl.

In a further emphasized group of compounds of the formula (I), $R^2$ and $R^3$ are each hydrogen, B is methoxy and A is 5-bromo-6-chloropyrid-3-yl.

In a further emphasized group of compounds of the formula (I), $R^2$ and $R^3$ are each hydrogen, B is methoxy and A is 6-chloro-5-methylpyrid-3-yl.

In a further emphasized group of compounds of the formula (I), $R^2$ and $R^3$ are each hydrogen, B is methoxy and A is 6-chloro-5-difluoromethylpyrid-3-yl.

In a further emphasized group of compounds of the formula (I), $R^1$ is difluoromethyl, $R^2$ and $R^3$ are each hydrogen and B is iso-propoxy.

In a further emphasized group of compounds of the formula (I), $R^1$ is 2-fluoroethyl, $R^2$ and $R^3$ are each hydrogen and B is iso-propoxy.

In a further emphasized group of compounds of the formula (I), $R^1$ is 2,2-difluoroethyl, $R^2$ and $R^3$ are each hydrogen and B is iso-propoxy.

In a further emphasized group of compounds of the formula (I), $R^1$ is methyl, $R^2$ and $R^3$ are each hydrogen and B is iso-propoxy.

In a further emphasized group of compounds of the formula (I), $R^1$ is cyclopropyl, $R^2$ and $R^3$ are each hydrogen and B is iso-propoxy.

In a further emphasized group of compounds of the formula (I), $R^1$ is 2-fluorocyclopropyl, $R^2$ and $R^3$ are each hydrogen and B is iso-propoxy.

In a further emphasized group of compounds of the formula (I), $R^1$ is methoxy, $R^2$ and $R^3$ are each hydrogen and B is iso-propoxy.

In a further emphasized group of compounds of the formula (I), $R^1$ is difluoromethyl, $R^2$ and $R^3$ are each hydrogen and B is methoxy.

In a further emphasized group of compounds of the formula (I), $R^1$ is 2-fluoroethyl, $R^2$ and $R^3$ are each hydrogen and B is methoxy.

In a further emphasized group of compounds of the formula (I), $R^1$ is 2,2-difluoroethyl, $R^2$ and $R^3$ are each hydrogen and B is methoxy.

In a further emphasized group of compounds of the formula (I), $R^1$ is methyl, $R^2$ and $R^3$ are each hydrogen and B is methoxy.

In a further emphasized group of compounds of the formula (I), $R^1$ is cyclopropyl, $R^2$ and $R^3$ are each hydrogen and B is methoxy.

In a further emphasized group of compounds of the formula (I), $R^1$ is 2-fluorocyclopropyl, $R^2$ and $R^3$ are each hydrogen and B is methoxy.

In a further emphasized group of compounds of the formula (I), $R^1$ is methoxy, $R^2$ and $R^3$ are each hydrogen and B is methoxy.

In a further emphasized group of compounds of the formula (I), $R^1$ is methyl, $R^2$ and $R^3$ are each hydrogen and B is iso-propoxy.

In a further emphasized group of compounds of the formula (I), $R^1$ is cyclopropyl, $R^2$ and $R^3$ are each hydrogen and B is iso-propoxy.

In a further emphasized group of compounds of the formula (I), $R^1$ is ethyl, $R^2$ and $R^3$ are each hydrogen and B is iso-propoxy.

In a further emphasized group of compounds of the formula (I), $R^1$ is methoxy, $R^2$ and $R^3$ are each hydrogen and B is iso-propoxy.

In a further emphasized group of compounds of the formula (I), $R^1$ is 2-fluorocyclopropyl, $R^2$ and $R^3$ are each hydrogen and B is iso-propoxy.

In a further emphasized group of compounds of the formula (I), $R^1$ is methyl, $R^2$ and $R^3$ are each hydrogen and B is methoxy.

In a further emphasized group of compounds of the formula (I), $R^1$ is cyclopropyl, $R^2$ and $R^3$ are each hydrogen and B is methoxy.

In a further emphasized group of compounds of the formula (I), $R^1$ is ethyl, $R^2$ and $R^3$ are each hydrogen and B is methoxy.

In a further emphasized group of compounds of the formula (I), $R^1$ is difluoromethyl, $R^2$ and $R^3$ are each hydrogen and D is methylcarbonyloxy.

In a further emphasized group of compounds of the formula (I), $R^1$ is 2-fluoroethyl, $R^2$ and $R^3$ are each hydrogen and D is methylcarbonyloxy.

In a further emphasized group of compounds of the formula (I), $R^1$ is 2,2-difluoroethyl, $R^2$ and $R^3$ are each hydrogen and D is methylcarbonyloxy.

In a further emphasized group of compounds of the formula (I), $R^1$ is difluoromethyl, $R^2$ and $R^3$ are each hydrogen and D is hydroxyl.

In a further emphasized group of compounds of the formula (I), $R^1$ is 2-fluoroethyl, $R^2$ and $R^3$ are each hydrogen and D is hydroxyl.

In a further emphasized group of compounds of the formula (I), $R^1$ is 2,2-difluoroethyl, $R^2$ and $R^3$ are each hydrogen and D is hydroxyl.

In a further emphasized group of compounds of the formula (I), $R^1$ is methyl, $R^2$ and $R^3$ are each hydrogen and B is D is methylcarbonyloxy.

In a further emphasized group of compounds of the formula (I), $R^1$ is cyclopropyl, $R^2$ and $R^3$ are each hydrogen and D is methylcarbonyloxy.

In a further emphasized group of compounds of the formula (I), $R^1$ is ethyl, $R^2$ and $R^3$ are each hydrogen and D is methylcarbonyloxy.

In a further emphasized group of compounds of the formula (I), $R^1$ is methyl, $R^2$ and $R^3$ are each hydrogen and D is hydroxyl.

In a further emphasized group of compounds of the formula (I), $R^1$ is cyclopropyl, $R^2$ and $R^3$ are each hydrogen and D is hydroxyl.

In a further emphasized group of compounds of the formula (I), $R^1$ is ethyl, $R^2$ and $R^3$ are each hydrogen and D is hydroxyl.

The radical definitions and explanations given above in general terms or given as preferred apply correspondingly to the end products and to the starting materials and intermedi ates. These radical definitions can be combined with one another as desired, i.e. including between the particular preferred ranges.

Preference is given in accordance with the invention to the (E)-isomers of the formula (I).

Salts suitable in accordance with the invention of the inventive compounds, for example salts with bases or acid addition salts, are all customary nontoxic salts, preferably agriculturally and/or physiologically acceptable salts, for example salts with bases or acid addition salts. Preference is given to salts with inorganic bases, for example alkali metal salts (e.g. sodium, potassium or caesium salts), alkaline earth metal salts (e.g. calcium or magnesium salts), ammonium salts or salts with organic bases, especially with organic amines, for example triethylammonium, dicyclohexylammonium, N,N'-dibenzylethylenediammonium, pyridinium, picolinium or ethanol-ammonium salts, salts with inorganic acids (e.g. hydrochlorides, hydrobromides, dihydrosulphates, trihydrosulphates, or phosphates), salts with organic carboxylic acids or organic sulphonic acids (e.g. formates, acetates, trifluoroacetates, maleates, tartrates, methanesulphonates, benzenesulphonates or 4-toluenesulphonates). As is well known, tertiary amines, for example some of the inventive compounds, form N-oxides, which likewise constitute inventive salts.

Preparation processes for the inventive compounds are described hereinafter, though they should not be interpreted in a restrictive manner. Further processes for preparing the inventive compounds can be derived in an analogous manner.

As shown in reaction scheme 1, inventive compounds can be obtained by using, in the process for preparing the inventive compounds, in reaction step (a), for example, prop-2-yn-1-yl acetate (as compound (II)) and iso-propyl chloroformate (as compound (III)). The iso-propyl 4-acetoxybut-2-ynecarboxylate thus obtained (as compound (IV)) is then reacted in reaction step (b) with, for example, N-[(6-chloropyridin-3-yl)methyl]methan-1-amine (as compound (V)).

Reaction scheme 1

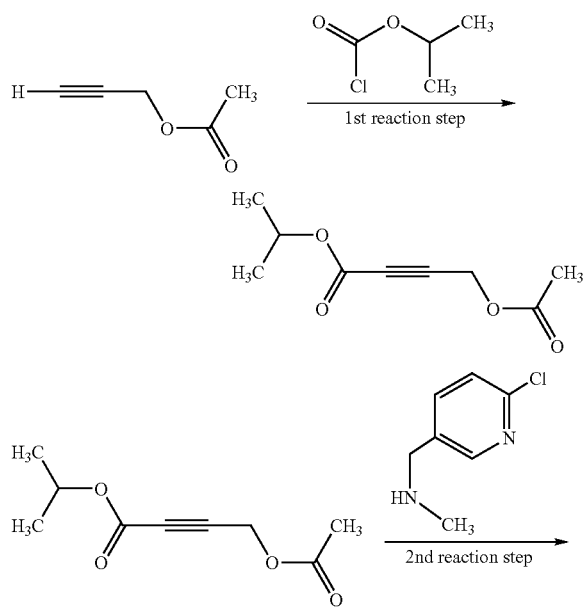

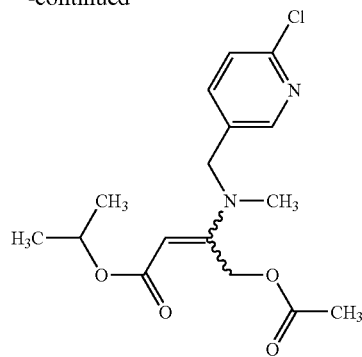

Some compounds of the formula (II) in which the D and $R^3$ radicals are each as defined above can be obtained commercially or synthesized by literature methods (cf., for example, compounds of the formula (II) in which D=O—CH(CH$_3$)$_2$, $R^3$=H: T. Takahashi, et al., *Macromolecules* 28, 866-869, 1995; D=O—CO—C(CH$_3$)$_3$, $R^3$=H: P. Prabhakar et al., *Chem. Lett.* 36, 732-733, 2007; D=O—CO—CH$_3$, $R^3$=CH$_3$: K Hiroi, F. Kato *Tetrahedron* 57, 1543-1550, 2001; D=O—CO—CH$_3$, $R^3$=C$_2$H$_5$; J. Kunes et al., *Coll. Czech. Chem. Commun.* 66, 1809-1830, 2001; C. Raminelli et al., *Tetrahedron: Asymmetry* 15, 3117-3122, 2004 [as the (S)-enantiomer]).

Some compounds of the formula (III) in which the B radical is as defined above and LG is, for example, halo-C$_1$-C$_8$-alkoxy, C$_1$-C$_8$-alkanoyloxy, mercapto, C$_1$-C$_8$-alkylthio, halo-C$_1$-C$_8$-alkylthio, halogen, especially C$_1$-C$_8$-alkoxy (e.g. methoxy), can be obtained commercially (e.g. chloroformic esters, acid chlorides) or by literature methods.

Some compounds of the formula (IV) in which the B, D and $R^3$ radicals are each as defined above, can be obtained commercially or by literature methods (cf., for example, compounds of the formula (IV) in which B=OCH$_2$C$_6$H$_5$, D=OH, $R^3$=H: B. M. C. Clasby et al., *Bioorg. Med. Chem. Lett.* 13, 3647-3651, 2007; B=OCH(CH$_3$)$_2$, D=O—CO—O—CH$_3$, $R^3$=H: R. Tayama, R. Hashimoto *Tetrahedron Lett.* 48, 7950-7952, 2007; B=OCH$_3$, D=O—CO—O—CH$_3$, $R^3$=H: O. David et al., *Heterocycles* 62, 839-846, 2004; B=OCH$_3$, D=O—CH$_2$—C≡CH, $R^3$=H: Y. Yamamoto *Tetrahedron Lett.* 62, 4294-4305, 2006; B=OCH$_3$, D=O—C(CH$_3$)$_3$, $R^3$=H: A. Covarrubias-Zuniga et al., *Synth. Commun.* 28, 3461-3469, 1998; B=OCH$_3$, D=O—CO—CH$_3$, $R^3$=H: N. Maezaki et al., *Tetrahedron: Asymmetry.* 13, 1961-1964, 2002; B=OCH$_3$, D=tetrahydro-2H-pyran-2-yl-oxy, $R^3$=H: R. Larock et al., *J. Org. Chem.* 48, 2151-2158, 1983; B=OC$_2$H$_5$, D=O—CO-aryl, $R^3$=H: Ch.-K. Jung et al., *J. Am. Chem. Soc.* 126, 4118-4119, 2004). In addition, the preparation and use of particular O-substituted 4-hydroxyalkyne-2-carboxylic esters as microbicides has become known (cf. B=OC$_2$H$_5$, D=O—CO-n-C$_4$H$_9$, $R^3$=CH$_3$: DE 4417752 A1).

Compounds of the formula (V) in which the A and $R^1$ radicals are each as defined above can also be prepared from compounds of the formula (VI) by literature methods (cf. N-[(6-chloropyridin-3-yl)methyl]-2,2-difluoroethan-1-amine, N-[(6-chloro-5-fluoropyridin-3-yl)methyl]-2,2-difluoroethan-1-amine: WO 2007/115646; WO 2008/009360; cf. scheme 2 below).

Some compounds of the formula (VI) are commercially available, known or can be prepared by known methods (e.g. 2-chloro-5-chloromethyl-1,3-thiazole: DE 3 631 538 (1988), EP 446 913 (1991), EP 780 384 (1997), EP 775 700 (1997), EP 794 180 (1997), WO 9 710 226 (1997); 6-chloro-3-chloromethylpyridine: DE 3 630 046 A1 (1988), EP 373 464 A2 (1990), EP 373 464 A2 (1990), EP 393 453 A2 (1990), EP 569 947 A1 (1993); 6-chloro-3-bromomethylpyridine: I. Cabanal-Duvillard et al., *Heterocycl. Commun.* 5, 257-262 (1999); 6-bromo-3-chloromethylpyridine, 6-bromo-3-hydroxymethylpyridine: U.S. Pat. No. 5,420,270 A (1995); 6-fluoro-3-chloromethylpyridine: J. A. Pesti et al., *J. Org. Chem.* 65, 7718-7722 (2000); 6-methyl-3-chloromethylpyridine: EP 302389 A2, E. v der Eycken et al., *J. Chem. Soc., Perkin Trans* 2 5, 928-937 (2002); 6-trifluoromethyl-3-chloromethylpyridine: WO 2004/082616 A2; 2-chloro-5-chloromethylpyrazine: JP 05239034 A2).

General ways of preparing compounds of the formula (VI) are shown in reaction scheme 2.

lag Stuttgart, p. 648; M. L. Moore in "The Leuckart Reaction" in: Organic Reactions, vol. 5, 2nd ed. 1952, New York, John Wiley & Sons, Inc. London) (cf., for example, also 3-fluoro-n-propylamine: U.S. Pat. No. 6,252,087 B1; 3,3-difluoro-prop-2-enylamine hydrochloride: WO 2001/007414 A1; 3,3-dichloro-prop-2-enylamine: DE 2747814); 2-chloro-2-fluorocyclopropylamine, 2,2-dichloro-cyclopropylamine: K. R. Gassen, B. Baasner, *J. Fluorine Chem.* 49, 127-139, 1990).

Alternatively, particular amino compounds of the formula (VIIa) in which $R^1$ is $CH_2$—R' (R'=halogenated radical; halogen=fluorine or chlorine) can also be obtained by reducing halogenated carboxamides (VIII) in the presence of suitable reducing agents (reaction scheme 4).

Reaction scheme 2

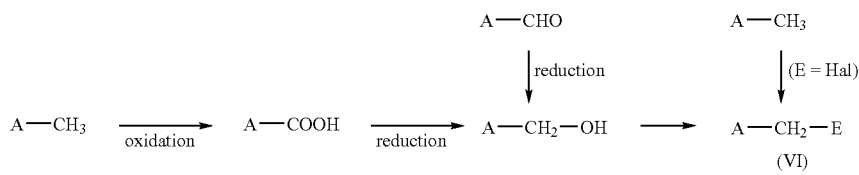

E = Hal, for example chlorine, bromine, iodine; O-tosyl, O-mesyl,
A = as defined above The heterocyclic carboxylic acid (A-COOH) can be converted by literature methods to the corresponding heterocyclic hydroxymethyl compounds (A-$CH_2$—OH), which are then converted by literature methods to activated heterocyclic hydroxymethyl compounds (A-$CH_2$-E, E=OTosyl, OMesyl) or heterocyclic halomethyl compounds (A-$CH_2$-E, E=Hal). The latter can also be obtained from corresponding methyl group-containing heterocycles (A-$CH_3$) using suitable literature halogenating agents.

To prepare compounds of the formula (V), it is advantageous that, for example, compounds of the formula (VI) in which the A and E radicals are each as defined above are reacted with compounds of the formula (VII) in which the $R^1$ radical is as defined above in the presence of diluents and in the presence of basic reaction auxiliaries (cf. N-alkylation, reaction scheme 3).

Reaction scheme 3

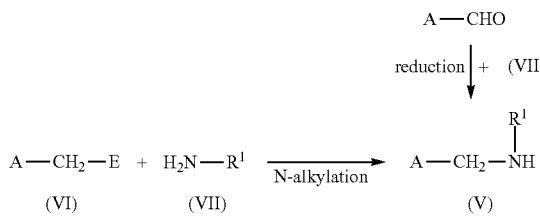

E = Hal, for example chlorine, bromine, iodine; O-tosyl, O-mesyl,
A = as defined above Some of the amino compounds of the formula (VII) can be obtained commercially (cf., for example, 2-fluoroethylamine or 2,2-difluoroethylamine) or in a manner known per se by the Leuckart-Wallach reaction (e.g. 2-fluoroethylamine: U.S. Pat. No. 4,030,994 (1977)); compounds of the formula (VII) in which $R^1$ is alkyl can likewise be obtained (primary amines: cf., for example, Houben-Weyl, Methoden der Organischen Chemie, vol. XI/1, 4th ed. 1957, Georg Thieme Ver- Reaction scheme 4

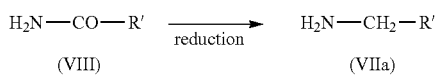

R' = halogenated radical

An example of a suitable reducing agent is the known borane-dimethyl sulphide complex (cf. also the preparation of 2-chloro-2-fluoroethan-1-amine from commercially available 2-chloro-2-fluoroacetamide).

Alternatively and in particular cases, preparation of compounds of the formula (V) from the corresponding aldehydes (A-CHO) and compounds of the formula (VII) by means of reductive amination is also possible (cf. Houben-Weyl, Methoden der Organischen Chemie, vol. XI/1, Georg Thieme Verlag Stuttgart, p. 602). Some of the aldehydes (A-CHO) are commercially available (cf., for example, 6-chloronicotinaldehyde, 6-fluoronicotinaldehyde, 6-bromonicotinaldehyde, 2-chloro-1,3-thiazole-5-carbaldehyde) or can be obtained by literature methods (cf., for example, 6-methylnicotinaldehyde: EP-A2-104876; 2-chloropyrazine-5-carboxaldehyde: DE 3314196 A1).

Reaction step (a) of the preparation process according to the invention is preferably performed in the presence of a basic reaction auxiliary and in the presence of diluents. Diluents are used in such an amount that the reaction mixture remains efficiently stirrable over the entire process. Suitable diluents are all inert organic solvents (e.g. halohydrocarbons, especially chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols such as methanol, ethanol, isopropanol, butanol); ethers (e.g. ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide); amines (e.g. trimethyl-, triethyl-, tripropyl-, tributylamine, N-methylmorpholine, pyridine and tetramethylenediamine); nitrohydrocarbons (e.g. nitromethane, nitroethane, nitropropane, nitrobenzene, chloronitrobenzene, o-nitrotoluene); nitriles (e.g. acetonitrile, propionitrile, butyronitrile, isobutyronitrile, benzonitrile, m-chlorobenzonitrile) and compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl, diethyl, dipropyl, dibutyl, diphenyl, dihexyl, methyl ethyl, ethyl propyl, ethyl isobutyl and pentamethylene sulphone; aliphatic, cycloaliphatic or aromatic hydrocarbons such as pentane, hexane, heptane, octane, nonane and technical-grade hydrocarbons; for example white spirits with components having boiling points in the range from about 40° C. to about 250° C., cymene, petroleum fractions within a boiling range from 70° C. to about 190° C., cyclohexane, methylcyclohexane, petroleum ether, ligroin, octane, benzene, toluene, chlorobenzene, bromobenzene, nitrobenzene, xylene; esters (e.g. methyl, ethyl, butyl, isobutyl acetate, and dimethyl, dibutyl, ethylene carbonate); amides (e.g. hexamethylenephosphoramide, formamide, N-methylformamide, N,N-dimethylformamide, N,N-dipropylformamide, N,N-dibutylformamide, N-methylpyrrolidone, N-methylcaprolactam, 1,3-dimethyl-3,4,5,6-tetrahydro-2(1H)-pyrimidine, octylpyrrolidone, octylcaprolactam, 1,3-dimethyl-2-imidazolidinedione, N-formyl-piperidine, N,N'-1,4-diformylpiperazine); ketones (e.g. acetone, acetophenone, methyl ethyl ketone, methyl butyl ketone). It is also possible to use mixtures of the aforementioned diluents.

In reaction step (a), the diluents used are preferably ethers, especially methyl tert-butyl ether and dipropyl ether, tetrahydrofuran and dioxane.

Reaction step (a) is preferably performed in the presence of a basis reaction auxiliary (i.e. auxiliary). Especially suitable are acid binders such as amines, especially tertiary amines, and alkali metal and alkaline earth metal compounds. Examples include the hydroxides, hydrides, oxides, amides and carbonates of lithium, sodium, potassium, magnesium, calcium and barium, and also further basic compounds such as amidine bases or guanidine bases such as 7-methyl-1,5,7-triazabicyclo[4.4.0]dec-5-ene (MTBD); diazabicyclo[4.3.0] nonene (DBN), diazabicyclo[2.2.2] octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine, tertiary amines such as triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, β-picoline, isoquinoline, pyrimidine, acridine, N,N,N',N'-tetramethylenediamine, N,N,N',N'-tetraethylenediamine, quinoxaline, N-propyldiisopropylamine, N-ethyl-N-diisopropylamine, N,N'-dimethylcyclohexylamine, 2,6-lutidine, 2,4-lutidine or triethyldiamine. Preferred basic auxiliaries are lithium bis(trimethylsilyl)amide or potassium bis(trimethylsilyl)-amide.

To perform reaction step (a), generally 0.5 to 4.0 mol, preferably 0.5 to 4.0 mol, more preferably 0.5 to 1.0 mol of compound of the general foimula (III) is used per mole of compound of the general formula (II).

After reaction, the entire reaction mixture of reaction step (a) is partitioned between water and a suitable halohydrocarbon, for example dichloromethane, and washed with dilute acid and base. The products obtained after workup can be purified by recrystallization, vacuum distillation or column chromatography (cf. also the preparation examples).

Reaction step (b) is advantageously performed in the presence of diluents, for which the diluents listed above can be used. Preference is given to using ethers such as tetrahydrofuran or dioxane.

In reaction step (b), generally 0.5 to 5.0 mol, preferably 0.5 to 3.0 mol, more preferably 0.5 to 1.5 mol and most preferably a slight excess of amino compound of the general formula (V) is used per mole of compound of the general formula (IV).

Diluents are advantageously used in such an amount that the reaction mixture remains efficiently stirrable over the entire process.

The reaction time of the process or of reaction step (a) or (b) is generally from 10 minutes to 48 hours. The reactions are effected at temperatures between −100° C. and +100° C., preferably between −80° C. and +80° C., particularly at −75° C. to room temperature.

It is possible in principle to work under standard pressure. Preference is given to working at standard pressure or at pressures up to 15 bar and optionally under protective gas atmosphere (nitrogen, helium or argon).

After the reaction has ended, the entire reaction mixture is concentrated. The products obtained after workup can be purified in a customary manner by recrystallization, vacuum distillation or column chromatography (cf. also the preparation examples).

The geometric (for example the E or Z isomers) and/or optically active isomers or corresponding isomer mixtures of the formula (I) can of course be separated by a suitable separation process, for example by means of column chromatography, optionally on a chiral phase, or by means of extraction processes (e.g. Craig partition).

To prepare the inventive compounds in which $R^2$ is halogen, it is alternatively also possible to react compounds of the formula (I) in which $R^2$ is hydrogen with halogenating agents in the presence of basic auxiliaries according to reaction scheme 5.

Reaction scheme 5:

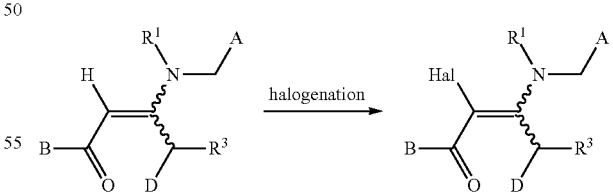

In the compounds of the formula (I) required as starting materials, A, B, D, $R^1$ and $R^3$ are each as defined above; the substituent $R^2$ is hydrogen.

The halogenation is advantageously performed in the presence of diluents.

The diluents are advantageously used in such an amount that the reaction mixture remains efficiently stirrable over the entire process. Suitable diluents are all organic solvents which are inert under the reaction conditions. Preferred diluents are nitriles such as acetonitrile, propionitrile, butyronitrile, isobutyronitrile, benzonitrile, m-chlorobenzonitrile; particularly preferred diluents are acetonitrile, propionitrile or butyronitrile.

Suitable halogenating agents are known to those skilled in the art. Preference is given to using N-halo compounds (e.g. N-haloamines such as 1-chloromethyl-4-fluorodiazoniabicyclo[2.2.2]octane bis(tetrafluoroborate) (Selectfluor®), N,N-dihaloamines, N-halocarboxamides, N-halo-carbamic esters, N-halourea, N-halosulphonylamides, N-halodisulphonylamides, N-halosulphonylimides such as N-fluorobis[(trifluoromethyl)sulphonyl]imide and N-halodicarboximides such as N-chlorophthalimide, N-bromophthalimide, N-iodophthalimide, N-chlorosuccinimide (NCS), N-bromosuccinimide (NBS), N-bromosaccharin or N-iodosuccinimide). Particular preference is given to N-halocarboxamides or 1-chloromethyl-4-fluorodiazoniabicyclo[2.2.2]octane bis (tetrafluoroborate)) (Selectfluor®).

The reaction time in this process is generally 10 minutes to 48 hours.

The reaction is effected at temperatures between −10° C. and +100° C., preferably between 0° C. and 60° C., more preferably between 10° C. and room temperature.

After the reaction has ended, the entire reaction mixture is concentrated. The products obtained after workup can be purified in a customary manner by recrystallization, vacuum distillation or column chromatography.

Here too, the halogenated geometric (for example the E or Z isomers) and/or optically active isomers or corresponding isomer mixtures of the formula (I) can of course be separated by a suitable separation process, for example by means of column chromatography, optionally on a chiral phase, or by means of extraction processes (e.g. Craig partition).

Salts of the inventive compounds are prepared by standard methods. Representative acid addition salts are, for example, those which are formed by reaction with inorganic acids, for example sulphuric acid, hydrochloric acid, hydrobromic acid, phosphoric acid, or organic carboxylic acids such as acetic acid, trifluoroacetic acid, citric acid, succinic acid, butyric acid, lactic acid, formic acid, fumaric acid, maleic acid, malonic acid, camphoric acid, oxalic acid, phthalic acid, propionic acid, glycolic acid, glutaric acid, stearic acid, salicylic acid, sorbic acid, tartaric acid, cinnamic acid, valeric acid, picric acid, benzoic acid, or organic sulphonic acids such as methanesulphonic acid and 4-toluenesulphonic acid.

Other representatives are salts of inventive compounds which are formed from organic bases, for example pyridine or triethylamine, or those which are formed from inorganic bases, for example hydrides, hydroxides or carbonates of sodium, potassium, lithium, calcium, magnesium or barium, when the compounds of the general formula (I) have a structural element capable of this salt formation.

Synthesis methods for preparation of heterocyclic N-oxides and tert-amines are known. They can be obtained with peroxy acids (e.g. peracetic acid and meta-chloroperbenzoic acid (MCPBA), hydrogen peroxide, alkyl hydroperoxides (e.g. tert-butyl hydroperoxide), sodium perborate and dioxiranes (e.g. dimethyldioxirane). These methods are described, for example, by T. L. Gilchrist, in *Comprehensive Organic Synthesis*, vol. 7, p. 748-750, 1992, S. V. Ley, (Ed.), Pergamon Press; M. Tisler, B. Stanovnik, in *Comprehensive Heterocyclic Chemistry*, vol. 3, p. 18-20, 1984, A. J. Boulton, A. McKillop, (Eds.), Pergamon Press; M. R. Grimmett, B. R. T. Keene in *Advances in Heterocyclic Chemistry*, vol. 43, p. 149-163, 1988, A. R. Katritzky, (Ed.), Academic Press; M. Tisler, B. Stanovnik, in *Advances in Heterocyclic Chemistry*, vol. 9, p. 285-291, 1968, A. R. Katritzky, A. J. Boulton (Eds.), Academic Press; G. W. H. Cheeseman, E. S. G. Werstiuk in *Advances in Heterocyclic Chemistry*, vol. 22, p. 390-392, 1978, A. R. Katritzky, A. J. Boulton, (Eds.), Academic Press.

The inventive compounds, given good plant tolerance, favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the *Anoplura (Phthiraptera)*, for example, *Damalinia* spp., *Haematopinus* spp., *Linognathus* spp., *Pediculus* spp., *Trichodectes* spp.

From the class of the *Arachnida*, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the *Bivalva*, for example, *Dreissena* spp.

From the order of the *Chilopoda*, for example, *Geophilus* spp., *Scutigera* spp.

From the order of the *Coleoptera*, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Deiniestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the *Collembola*, for example, *Onychiurus armatus*.

From the order of the *Dermaptera*, for example, *Forficula auricularia*.

From the order of the *Diplopoda*, for example, *Blaniulus guttulatus*.

From the order of the *Diptera*, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the *Gastropoda*, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudospiralis, Trichostrongulus* spp., *Trichuris trichuria, Wuchereria bancrofti*.

It is additionally possible to control protozoa, such as *Eimeria*.

From the order of the *Heteroptera*, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the *Homoptera*, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii*.

From the order of the *Hymenoptera*, for example, *Diprion* spp., *Hoplocampa* spp., *Lasius* spp., *Monomorium pharaonis, Vespa* spp.

From the order of the *Isopoda*, for example, *Armadillidium vulgare, Oniscus asellus, Porcellio scaber*.

From the order of the *Isoptera*, for example, *Reticulitermes* spp., *Odontotermes* spp.

From the order of the *Lepidoptera*, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the *Orthoptera*, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria*.

From the order of the *Siphonaptera*, for example, *Ceratophyllus* spp., *Xenopsylla cheopis*.

From the order of the *Symphyla*, for example, *Scutigerella immaculata*.

From the order of the *Thysanoptera*, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the *Thysanura*, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

If appropriate, the inventive compounds can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active ingredients.

The active ingredients can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active ingredient, synthetic materials impregnated with active ingredient, fertilizers and microencapsulations in polymeric substances.

These formulations are produced in a known manner, for example by mixing the active ingredients with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Useful solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol POE and/or POP ethers, acid and/or POP-POE esters, alkyl aryl and/or POP-POE ethers, fat and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. In addition, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use dyes such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

Further possible additives are perfumes, mineral or vegetable, optionally modified oils, waxes and nutrients (including trace nutrients), such as salts of iron, manganese, boron, copper, cobalt, molybdenum and zinc.

Stabilizers such as low-temperature stabilizers, preservatives, antioxidants, light stabilizers or other agents which improve chemical and/or physical stability may also be present.

The formulations generally comprise between 0.01 and 98% by weight of active ingredient, preferably between 0.5 and 90%.

The inventive active ingredient can be used in its commercially available formulations and in the use forms, prepared from these formulations, as a mixture with other active ingredients, such as insecticides, attractants, sterilizing agents, bactericides, acaricides, nematicides, fungicides, growth-regulating substances, herbicides, safeners, fertilizers or semiochemicals.

Particularly favourable mixing components are, for example, the following compounds:

Fungicides:
(1) Nucleic acid synthesis inhibitors, for example benalaxyl, benalaxyl-M, bupirimate, clozylacon, dimethirimol, ethirimol, furalaxyl, hymexazol, metalaxyl, metalaxyl-M, ofurace, oxadixyl and oxolinic acid.
(2) Mitosis and cell division inhibitors, for example benomyl, carbendazim, chlorfenazole, diethofencarb, ethaboxam, fuberidazole, pencycuron, thiabendazole, thiophanate, thiophanate-methyl and zoxamide.
(3) Respiration inhibitors (inhibitors of the respiratory chain), for example diflumetorim as inhibitor which acts on complex I of the respiratory chain; bixafen, boscalid, carboxin, fenfuram, flutolanil, fluopyram, furametpyr, furmecyclox, isopyrazam (mixture of the syn-epimeric racemate 1RS, 4SR,9RS and the anti-epimeric racemate 1RS,4SR,9SR), isopyrazam (syn-epimeric racemate 1RS,4SR,9RS), isopyrazam (syn-epimeric enantiomer 1R,4S,9R), isopyrazam (syn-epimeric enantiomer 1S,4R,9S), isopyrazam (anti-epimeric racemate 1RS,4SR,9SR), isopyrazam (anti-epimeric enantiomer 1R,4S,9S), isopyrazam (anti-epimeric enantiomer 1S,4R,9R),
mepronil, oxycarboxin, penflufen, penthiopyrad, sedaxane, thifluzamid as inhibitors which act on complex II of the respiratory chain; amisulbrom, azoxystrobin, cyazofamid, dimoxystrobin, enestroburin, famoxadone, fenamidone, fuoxastrobin, kresoxim-methyl, metominostrobin, orysastrobin, picoxystrobin, pyraclostrobin, pyraoxystrobin, pyrametostrobin, pyribencarb, trifloxystrobin as inhibitors which act on complex III of the respiratory chain.
(4) Decouplers, for example binapacryl, dinocap, fluazinam and meptyldinocap.
(5) ATP production inhibitors, for example fentin acetate, fentin chloride, fentin hydroxide and silthiofam.

(6) Amino acid and protein biosynthesis inhibitors, for example andoprim, blasticidin-S, cyprodinil, kasugamycin, kasugamycin hydrochloride hydrate, mepanipyrim and pyrimethanil.
(7) Signal transduction inhibitors, for example fenpiclonil, fludioxonil and quinoxyfen.
(8) Lipid and membrane synthesis inhibitors, for example biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl and vinclozolin.
(9) Ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, viniconazole and voriconazole.
(10) Cell wall synthesis inhibitors, for example benthiavalicarb, dimethomorph, flumorph, iprovalicarb, mandipropamid, polyoxins, polyoxorim, prothiocarb, validamycin A and valefenalate.
(11) Melanin biosynthesis inhibitors, for example carpropamid, diclocymet, fenoxanil, phthalide, pyroquilon and tricyclazole.
(12) Resistance inductors, for example acibenzolar-S-methyl, probenazole and tiadinil.
(13) Compounds with multi-site activity, for example Bordeaux mixture, captafol, captan, chlorothalonil, copper naphthenate, copper oxide, copper oxychloride, copper preparations such as, for example, copper hydroxide, copper sulphate, dichlofluanid, dithianon, dodine and its free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations such as, for example, calcium polysulphide, thiram, tolylfluanid, zineb and ziram.
(14) Further compounds, for example 2,3-dibutyl-6-chlorothieno[2,3-d]pyrimidin-4(3H)-one, ethyl (2Z)-3-amino-2-cyano-3-phenylprop-2-enoate, N-[2-(1,3-dimethylbutyl)phenyl]-5-fluoro-1,3-dimethyl-1H-pyrazole-4-carboxamide, 3-(difluoromethyl)-1-methyl-N-(3',4',5'-trifluorobiphenyl-2-yl)-1H-pyrazole-4-carboxamide, 3-(difluoromethyl)-N-[4-fluoro-2-(1,1,2,3,3,3-hexafluoropropoxy)-phenyl]-1-methyl-1H-pyrazole-4-carboxamide, (2E)-2-(2-{[6-(3-chloro-2-methylphenoxy)-5-fluoropyrimidin-4-yl]oxy}phenyl)-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, N-(3-ethyl-3,5,5-trimethylcyclohexyl)-3-(formylamino)-2-hydroxybenzamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N-ethyl-N-methyl-N'-{2-methyl-5-(trifluoromethyl)-4-[3-(trimethylsilyl)propoxy]phenyl}imidoformamide, N'-{5-(difluoromethyl)-2-methyl-4-[3-(trimethylsilyl)propoxy]phenyl}-N-ethyl-N-methylimidoformamide, O-{1-[(4-methoxyphenoxy)methyl]-2,2-dimethylpropyl}1H-imidazole-1-carbothioate, N-[2-(4-{[3-(4-chlorophenyl)prop-2-yn-1-yl]oxy}-3-methoxyphenyl)ethyl]-$N^2$-(methylsulphonyl)valinamide, 5-chloro-7-(4-methylpiperidin-1-yl)-6-(2,4,6-trifluorophenyl)[1,2,4]triazolo[1,5-a]pyrimidine, 5-amino-1,3,4-thiadiazole-2-thiole, propamocarb-fosetyl, 1-[(4-methoxyphenoxy)methyl]-2,2-dimethylpropyl 1H-imidazole-1-carboxylate, 1-methyl-N-[2-(1,1,2,2-tetrafluoroethoxy)phenyl]-3-(trifluoromethyl)-1H-pyrazole-4-carboxamide, 2,3,5,6-tetrachloro-4-(methylsulphonyl)pyridine, 2-butoxy-6-iodo-3-propyl-4H-chromen-4-one, 2-phenylphenol and its salts, 3-(difluoromethyl)-1-methyl-N-[2-(1,1,2,2-tetrafluoroethoxy)phenyl]-1H-pyrazole-4-carboxamide, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 8-hydroxyquinoline, 8-hydroxyquinoline sulphate, tebufloquin, 5-methyl-6-octyl-3,7-dihydro[1,2,4]triazolo[1,5-a]pyrimidine-7-amine, 5-ethyl-6-octyl-3,7-dihydro[1,2,4]triazolo[1,5-a]pyrimidine-7-amine, ametoctradin, benthiazol, bethoxazin, capsimycin, carvone, chinomethionat, chloroneb, cufraneb, cyflufenamide, cymoxanil, cyprosulfamide, dazomet, debacarb, dichlorophen, diclomezine, dicloran, difenzoquat, difenzoquat methylsulphate, diphenylamine, ecomat, ferimzone, flumetover, fluopicolide, fluoromide, flusulfamide, flutianil, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl}-3-methoxyacrylate, methyl isothiocyanate, metrafenone, (5-chloro-2-methoxy-4-methylpyridin-3-yl)(2,3,4-trimethoxy-6-methylphenyl)methanone, mildiomycin, tolnifanide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(Z)-[(cyclopropylmethoxy)imino][6-(difluoromethoxy)-2,3-difluorophenyl]methyl}-2-phenylacetamide, N-{(E)-[(cyclopropylmethoxy)imino][6-(difluoromethoxy)-2,3-difluorophenyl]methyl}-2-phenylacetamide, natamycin, nickel dimethyldithiocarbamate, nitrothal-isopropyl, octhilinone, oxamocarb, oxyfenthiin, pentachlorophenol and its salts, phenazine-1-carboxylic acid, phenothrin, phosphoric acid and its salts, propamocarb fosetylate, propanosine-sodium, proquinazid, pyrrolnitrin, quintozene, S-prop-2-en-1-yl 5-amino-2-(1-methylethyl)-4-(2-methylphenyl)-3-oxo-2,3-dihydro-1H-pyrazole-1-carbothioate, tecloftalam, tecnazene, triazoxide, trichlamide, 5-chloro-N'-phenyl-N'-prop-2-yn-1-ylthiophene-2-sulphonohydrazide, zarilamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, 3-(difluoromethyl)-N-[4-fluoro-2-(1,1,2,3,3,3-hexafluoropropoxy)phenyl]-1-methyl-1H-pyrazole-4-carboxamide and pentyl {6-[({[(1-methyl-1H-tetrazol-5-yl)(phenyl)methylidene]amino}oxy)methyl]pyridin-2-yl}carbamate.

Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

The active ingredients specified in this description by their "common name" are known, for example, from "The Pesticide Manual", 14th Ed., British Crop Protection Council 2006, and from the Web page http://www.alanwood.net/pesticides/.

(1) Acetylcholinesterase (AChE) inhibitors, for example carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triazamate, triclorfon and vamidothion.

(2) GABA-gated chloride channel antagonists, for example organochlorines, for example chlordane and endosulfan (alpha-); or fiproles (phenylpyrazoles), for example ethiprole, fipronil, pyrafluprole and pyriprole.

(3) Sodium channel modulators/voltage-dependent sodium channel blockers, for example pyrethroids, for example acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomeres], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; or DDT; or methoxychlor.

(4) Nicotinergic acetylcholine receptor agonists, for example neonicotinoids, for example acetamiprid, clothianidin, dinotefuran, imidacloprid, nitenpyram, thiacloprid, thiamethoxam, AKD-1022, imidaclothiz; or nicotine.

(5) Allosteric acetylcholine receptor modulators (agonists), for example spinosyns, for example spinetoram and spinosad.

(6) Chloride channel activators, for example avermectins/milbemycins, for example abamectin, emamectin benzoate, lepimectin and milbemectin.

(7) Juvenile hormone analogues, for example hydroprene, kinoprene, methoprene; or fenoxycarb; pyriproxyfen.

(8) Active ingredients with unknown or non-specific mechanisms of action, for example fumigants, for example methyl bromide and other alkyl halides; or chloropicrin; sulphuryl fluoride; borax; tartar emetic.

(9) Selective antifeedants, for example pymetrozine; or flonicamid.

(10) Mite growth inhibitors, for example clofentezine, diflovidazin, hexythiazox, etoxazole.

(11) Microbial disruptors of the insect gut membrane, for example *Bacillus thuringiensis* subsp. *israelensis, Bacillus sphaericus, Bacillus thuringiensis* subsp. *aizawai, Bacillus thuringiensis* subsp. *kurstaki, Bacillus thuringiensis* subsp. *tenebrionis*, and BT plant proteins, for example Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron; or organotin compounds, for example azocyclotin, cyhexatin, fenbutatin oxide; or propargite; tetradifon.

(13) Oxidative phoshorylation decouplers acting by interrupting the H proton gradient, for example chlorfenapyr and DNOC.

(14) Nicotinergic acetylcholine receptor antagonists, for example bensultap, cartap (hydrochloride), thiocylam, and thiosultap (sodium).

(15) Chitin biosynthesis inhibitors, type 0, for example benzoylureas, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting disruptors, for example cyromazine.

(18) Ecdysone agonists/disruptors, for example diacylhydrazines, for example chromafenozide, halofenozide, methoxyfenozide and tebufenozide.

(19) Octopaminergic agonists, for example amitraz.

(20) Site III electron transport inhibitors/site II electron transport inhibitors, for example hydramethylnone; acequinocyl; fluacrypyrim; or cyflumetofen and cyenopyrafen.

(21) Electron transport inhibitors, for example site I electron transport inhibitors, from the group of the METI acaricides, for example fenazaquin, fenpyroximate, pyrimidifen, pyridaben, tebufenpyrad, tolfenpyrad; or rotenone (Derris).

(22) Voltage-dependent sodium channel blockers, for example indoxacarb; metaflumizone.

(23) Inhibitors of acetyl-CoA carboxylase, for example tetronic acid derivatives, for example spirodiclofen and spiromesifen; or tetramic acid derivatives, for example spirotetramat.

(24) Site IV electron transport inhibitors, for example phosphines, for example aluminium phosphide, calcium phosphide, phosphine, zinc phosphide; or cyanide.

(25) Ryanodine receptor effectors, for example diamides, for example chlorantraniliprole (Rynaxypyr), cyantraniliprole (Cyazypyr) and flubendiamide.

Further active ingredients with unknown mechanism of action, for example azadirachtin, amidoflumet, benzoximate, bifenazate, chinomethionat, cryolite, dicofol, flufenerim, pyridalyl and pyrifluquinazon; or the known active compounds below 4-{[(6-bromopyrid-3-yl)methyl](2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2-fluoroethyl)amino furan-2(5H)-one (known from WO 2007/115644), 4-{[(6-chloropyrid-3-yl)methyl](2-fluoroethyl)amino furan-2(5H)-one (known from WO 2007/115644), 4-{[(6-chloropyrid-3-yl)methyl](2,2-difluoroethyl)amino}furan-2(5H)-one (known from WO 2007/115644), 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [(6-chloropyridin-3-yl)methyl](methyl)oxido-$\lambda^4$-sulphanylidenecyanamide (known from WO 2007/149134), [1-(6-chloropyridin-3-yl)ethyl](methyl)oxido-$\lambda^4$-sulphanylidenecyanamide (known from WO 2007/149134) and its diastereomers (A) and (B)

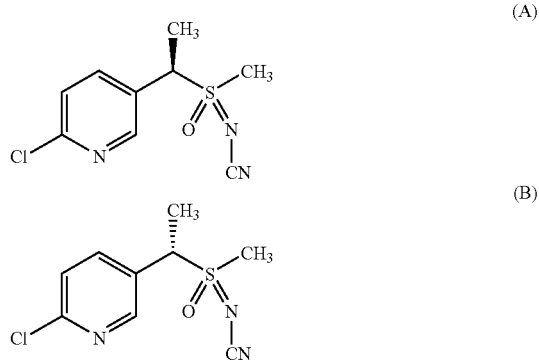

(likewise known from WO 2007/149134), [(6-trifluoromethylpyridin-3-yl)methyl](methyl)oxido-$\lambda^4$-sulphanylidenecyanamide (known from WO 2007/095229), sulfoxaflor (likewise known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911) and 1-{2,4-dimethyl-5-[(2,2,2-trifluoroethyl)sulphinyl]phenyl}-3-(trifluoromethyl)-1H-1,2,4-triazole (known from WO 1999/55668).

When used as insecticides, the inventive active ingredients can also be present in their commercially available formulations and in the use forms, prepared from these formulations, as a mixture with synergists. Synergists are compounds which increase the action of the active ingredients, without it being necessary for the synergist added to be active itself.

When used as insecticides, the inventive active ingredients can also be present in their commercially available formulations and in the use forms, prepared from these formulations, as a mixture with inhibitors which reduce degradation of the active ingredient after use in the environment of the plant, on the surface of parts of plants or in plant tissues.

The active ingredient content of the use forms prepared from the commercially available formulations can vary within wide limits. The active ingredient concentration of the use forms can be from 0.00000001 to 95% by weight of active ingredient, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active ingredients is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

Treatment according to the invention of the plants and plant parts with the active ingredient combinations is carried out directly or by allowing the compounds to act on the surroundings, habitat or storage space by the customary treatment methods, for example by immersion, spraying, evaporation, fogging, scattering, painting on, and, in the case of propagation material, in particular in the case of seeds, also by applying one or more coats.

The inventive mixtures are particularly suitable for treating seed. Here, the combinations according to the invention mentioned above as preferred or particularly preferred may be mentioned as being preferred. Thus, a large part of the damage to crop plants which is caused by pests occurs as early as when the seed is attacked during storage and after the seed is introduced into the soil, and also during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of pests by treating the seeds of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants. It is also desirable to optimize the amount of active ingredient employed in such a way as to provide maximum protection for the seed and the germinating plant from attack by pests, but without damaging the plant itself by the active ingredient employed. In particular, methods for the treatment of seed should also take into consideration the intrinsic insecticidal properties of transgenic plants in order to achieve optimum protection of the seed and the geiiiiinating plant with a minimum of crop protection agents being employed.

The present invention therefore in particular also relates to a method for the protection of seed and germinating plants from attack by pests, by treating the seed with an inventive composition. The invention likewise relates to the use of the inventive compositions for the treatment of seed for protecting the seed and the resultant plant from pests. The invention further relates to seed which has been treated with an inventive composition so as to afford protection from pests.

One of the advantages of the present invention is that the particular systemic properties of the inventive compositions mean that treatment of the seed with these compositions not only protects the seed itself, but also the resulting plants after emergence, from pests. In this manner, the immediate treatment of the crop at the time of sowing or shortly thereafter can be dispensed with.

A further advantage is the synergistically increased insecticidal activity of the inventive compositions in comparison with the individual insecticidal active ingredient, which exceeds the anticipated activity of the two active ingredients when applied individually. Also advantageous is the synergistically increased fungicidal activity of the inventive compositions in comparison with the individual fungicidal active ingredient, which exceeds the anticipated activity of the active ingredient when applied individually. This makes possible an optimization of the amount of active ingredient employed.

Furthermore, it must be considered as advantageous that the inventive mixtures can also be employed in particular in transgenic seed, the plants arising from this seed being capable of expressing a protein directed against pests. By treating such seed with the inventive compositions, certain pests can be controlled merely by the expression of the, for example, insecticidal protein, and additionally be protected by the inventive compositions against damage.

The inventive compositions are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, sorghum and millet, wheat, barley, oats, rye, sunflower, tobacco, potatoes or vegetables (for example tomatoes, cabbage plants). The inventive compositions are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with an inventive composition is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus*, *Rhizobium*, *Pseudomonas*, *Serratia*, *Trichoderma*, *Clavibacter*, *Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from Bacillus thuringiensis.

In the context of the present invention, the inventive composition is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the inventive composition applied to the seed and/or the amount of further additives is chosen in such a way that the germination of the seed is not adversely affected, or that the resulting plant is not damaged. This must be borne in mind in particular in the case of active ingredients which may have phytotoxic effects at certain application rates.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processibility of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processibility of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active ingredients. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins.

Traits that are also particularly emphasized are the increased tolerance of the plants to certain herbicidally active ingredients, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), Knock-Out® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active ingredient inventive mixtures. The preferred ranges stated above for the active ingredients or mixtures also apply to the treatment of these plants. Particular emphasis is given to the treatment of plants with the compounds or mixtures specifically mentioned in the present text.

The inventive active ingredients act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the *Anoplurida*, for example, *Haematopinus* spp., *Linognathus* spp., *Pediculus* spp., *Phtirus* spp., *Solenopotes* spp.

From the order of the *Mallophagida* and the suborders *Amblycerina* and *Ischnocerina*, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the *Diptera* and the suborders *Nematocerina* and *Brachycerina*, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the *Siphonapterida*, for example, *Pulex* spp., *Ctenocephalides* spp., *Xenopsylla* spp., *Ceratophyllus* spp.

From the order of the *Heteropterida*, for example, *Cimex* spp., *Triatoma* spp., *Rhodnius* spp., *Panstrongylus* spp.

From the order of the *Blattarida*, for example, *Blatta orientalis*, *Periplaneta americana*, *Blattela germanica*, *Supella* spp.

From the subclass of the *Acari* (*Acarina*) and the orders of the Meta- and *Mesostigmata*, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the *Actinedida* (*Prostigmata*) and *Acaridida* (*Astigmata*), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The inventive active ingredients of the formula (I) are also suitable for controlling arthropods which infest agricultural productive livestock, for example cattle, sheep, goats, horses, pigs, donkeys, camels, buffalo, rabbits, chickens, turkeys, ducks, geese and bees, other pets, for example dogs, cats, caged birds and aquarium fish, and also so-called test animals, for example hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the inventive active ingredients.

The inventive active ingredients are used in the veterinary sector and in animal husbandry in a known manner by enteral administration in the form of, for example, tablets, capsules, potions, drenches, granules, pastes, boluses, the feed-through process and suppositories, by parenteral administration, for example by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active ingredient, such as collars, ear marks, tail marks, limb bands, halters, marking devices and the like.

When used for cattle, poultry, pets and the like, the active ingredients of the formula (I) can be used as formulations (for example powders, emulsions, free-flowing compositions), which comprise the active ingredients in an amount of 1 to 80% by weight, directly or after 100 to 10 000-fold dilution, or they can be used as a chemical bath.

It has also been found that the inventive compounds also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pectinicornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The inventive compounds can likewise be employed for protecting objects which come into contact with seawater or brackish water, such as hulls, screens, nets, buildings, moorings and signalling systems, against fouling.

Furthermore, the inventive compounds, alone or in combinations with other active ingredients, may be employed as antifouling agents.

In domestic, hygiene and stored-product protection, the active ingredients are also suitable for controlling animal pests, in particular insects, arachnids and mites, which are found in enclosed spaces such as, for example, dwellings, factory halls, offices, vehicle cabins and the like. They can be used to control these pests alone or in combination with other active ingredients and auxiliaries in domestic insecticide products. They are active against sensitive and resistant species and against all developmental stages. These pests include:

From the order of the *Scorpionidea*, for example, *Buthus occitanus.*

From the order of the *Acarina*, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the *Araneae*, for example, *Aviculariidae, Araneidae.*

From the order of the *Opiliones*, for example, *Pseudoscorpiones chelifer, Pseudoscorpiones cheiridium, Opiliones phalangium.*

From the order of the *Isopoda*, for example, *Oniscus asellus, Porcellio scaber.*

From the order of the *Diplopoda*, for example, *Blaniulus guttulatus, Polydesmus* spp.

From the order of the *Chilopoda*, for example, *Geophilus* spp.

From the order of the *Zygentoma*, for example, *Ctenolepisma* spp., *Lepisma saccharina, Lepismodes inquilinus.*

From the order of the *Blattaria*, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the *Saltatoria*, for example, *Acheta domesticus.*

From the order of the *Dermaptera*, for example, *Forficula auricularia.*

From the order of the *Isoptera*, for example, *Kalotermes* spp., *Reticulitermes* spp.

From the order of the *Psocoptera*, for example, *Lepinatus* spp., *Liposcelis* spp.

From the order of the *Coleoptera*, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the *Diptera*, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the *Lepidoptera*, for example, *Achroia grisella, Galleria mellonella, Plodia interpunctella, Tinea cloacella, Tinea pellionella, Tineola bisselliella.*

From the order of the *Siphonaptera*, for example, *Ctenocephalides canis, Ctenocephalides felis, Pulex irritans, Tunga penetrans, Xenopsylla cheopis.*

From the order of the *Hymenoptera*, for example, *Camponotus herculeanus, Lasius fuliginosus, Lasius niger, Lasius umbratus, Monomorium pharaonis, Paravespula* spp., *Tetramorium caespitum.*

From the order of the *Anoplura*, for example, *Pediculus humanus capitis, Pediculus humanus corporis, Pemphigus* spp., *Phylloera vastatrix, Phthirus pubis.*

From the order of the *Heteroptera*, for example, *Cimex hemipterus, Cimex lectularius, Rhodinus prolixus, Triatoma infestans.*

In the field of household insecticides, they are used alone or in combination with other suitable active ingredients, such as phosphoric esters, carbamates, pyrethroids, neonicotinoids, growth regulators or active ingredients from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

PREPARATION EXAMPLES

Example 1 iso-Propyl 4-acetoxy-3-[(6-chloropyrid-3-ylmethyl)amino]but-2-enecarboxylate

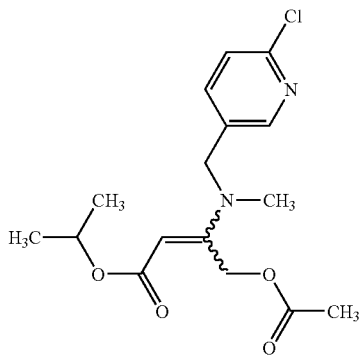

To an initial charge of 124 mg (0.672 mmol) of iso-propyl 4-acetoxybut-2-ynecarboxylate in 5 ml of anhydrous tetrahydrofuran (THF) are added dropwise 116 mg (0.739 mmol) of 1-(6-chloropyridin-3-yl)-N-methylmethanamine, dissolved in 1 ml of anhydrous THF, at room temperature. The reaction mixture is stirred at room temperature for 16 h and concentrated under reduced pressure. Subsequently, the residue is taken up with toluene and washed successively with dilute aqueous sulphuric acid and sodium hydrogencarbonate solution. After drying over magnesium sulphate and concentrating the organic phase under reduced pressure, 120 mg (50% of theory) of iso-propyl 4-acetoxy-3-[(4-chlorobenzyl)(methyl)amino]but-2-enecarboxylate are obtained.

$^1$H NMR (CD$_3$CN, δ, ppm)=8.21 (m, 1H), 7.56 (m, 1H), 7.36 (m, 1H), 5.45 (s, 2H), 4.91 (sept., 1H), 4.70 (s, 1H), 4.46 (s, 2H), 2.86 (s, 3H), 1.92 (s, 3H), 1.17 (d, 6H).

Table 1 below lists further compounds of the general formula (I).

TABLE 1

Compounds of the formula (Ia) in which A is 6-chloropyrid-3-yl

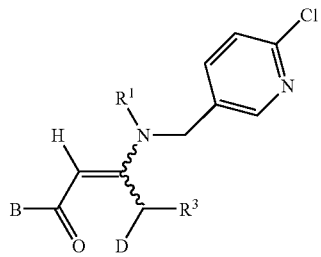

(Ia)

| Ex. No. | B | R$^1$ | R$^3$ | D | Physical data: $^1$H NMR, δ [ppm]$^a$ |
|---|---|---|---|---|---|
| 2 | OCH$_3$ | H | CH$_3$ | O—CO—O—CH$_3$ | 8.18 (m, 1H), 7.53 (m, 1H), 7.35 (m, 1H), 7.18 (dd, 1H), 4.67 (d, 1H), 4.67 (s, 1H), 4.42 (d, 1H), 3.66 (s, 3H), 3.57 (s, 3H), 2.82 (s, 3H), 1.57 (d, 3H) |
| 3 | OCH$_3$ | H | CH$_3$ | O—CO—CH$_3$ | 8.19 (m, 1H), 7.53 (m, 1H), 7.36 (m, 1H), 7.28 (dd, 1H), 4.73 (d, 1H), 4.63 (s, 1H), 4.46 (d, 1H), 3.56 (s, 3H), 2.84 (s, 3H), 1.80 (s, 3H), 1.51 (d, 3H) |
| 4 | OCH$_3$ | H | H | O—CH$_2$—C≡CH | 8.21 (m, 1H), 7.57 (m, 1H), 7.34 (m, 1H), 4.96 (s, 2H), 4.70 (s, 1H), 4.53 (s, 2H), 4.20 (d, 2H), 3.56 (s, 3H), 2.86 (s, 3H), 2.65 (t, 1H) |
| 5 | OCH$_3$ | H | H | O—CH(CH$_3$)$_2$ | 8.20 (m, 1H), 7.55 (m, 1H), 7.36 (m, 1H), 5.45 (s, 2H), 4.75 (s, 1H), 4.53 (s, 2H), 3.55 (s, 3H), 2.88 (s, 3H), 2.46 (sept., 1H), 1.07 (d, 6H) |
| 6 | OCH$_3$ | H | H | O-Cypr | 8.21 (m, 1H), 7.56 (m, 1H), 7.36 (m, 1H), 5.47 (s, 2H), 4.76 (s, 1H), 4.48 (s, 2H), 3.56 (s, 3H), 2.88 (s, 3H), 1.47 (m, 1H), 0.81 (m, 4H) |
| 7 | OC$_2$H$_5$ | H | H | O—CO—CH$_3$ | 8.21 (m, 1H), 7.56 (m, 1H), 7.36 (m, 1H), 5.46 (s, 2H), 4.74 (s, 1H), 4.47 (s, 2H), 4.03 (q, 2H), 2.87 (s, 3H), 2.01 (s, 3H), 1.18 (t, 3H) |
| 8 | OCH(CH$_3$)$_2$ | H | H | O—CO—CH$_3$ | 8.03 (m, 1H), 7.38 (m, 1H), 7.18 (m, 1H), 5.27 (s, 2H), 4.59 (s, 1H), 4.29 (s, 2H), 3.61 (d, 2H), 2.69 (s, 3H), 1.68 (m, 1H), 0.72 (d, 6H) |
| 9 | OCH$_3$ | H | H | O—CO—C(CH$_3$)$_3$ | 8.20 (m, 1H), 7.55 (m, 1H), 7.35 (m, 1H), 5.43 (s, 2H), 4.75 (s, 1H), 4.49 (s, 2H), 3.55 (s, 3H), 2.89 (s, 3H), 1.13 (s, 9H) |

TABLE 1-continued

Compounds of the formula (Ia) in which A is 6-chloropyrid-3-yl (Ia)

| Ex. No. | B | R¹ | R³ | D | Physical data: $^1$H NMR, δ [ppm]$^a$ |
|---|---|---|---|---|---|
| 10 | OCH$_3$ | H | H | O—CO—CH$_3$ | 8.20 (m, 1H), 7.56 (m, 1H), 7.35 (m, 1H), 5.53 (s, 2H), 4.76 (s, 1H), 4.48 (s, 2H), 3.71 (s, 3H), 3.56 (s, 3H), 2.87 (s, 3H) |
| 11 | OCH$_3$ | C$_2$H$_5$ | H | O—CO—CH$_3$ | 8.21 (m, 1H), 7.57 (m, 1H), 7.35 (m, 1H), 5.43 (s, 2H), 4.71 (s, 1H), 4.46 (s, 2H), 3.53 (s, 3H), 3.32 (q, 2H), 1.95 (s, 3H), 1,13 (t, 3H) |
| 12 | OCH$_3$ | Cypr | H | O—CO—CH$_3$ | 8.22 (m, 1H), 7.58 (m, 1H), 7.21 (m, 1H), 5.41 (s, 2H), 5.14 (s, 1H), 4.50 (s, 2H), 3.57 (s, 3H), 2.47 (m, 1H), 2.01 (s, 3H), 0.81 (m, 2H), 0.66 (m, 2H) |
| 13 | OCH$_3$ | CH$_3$ | H | O—CO—C$_2$H$_5$ | 8.05 (m, 1H), 7.41 (m, 1H), 7.20 (m, 1H), 5.32 (s, 2H), 4.60 (s, 1H), 4.32 (s, 3H), 3.40 (s, 3H), 2.72 (s, 3H), 2.07 (q, 2H), 0.87 (t, 3H) |
| 14 | OCH$_3$ | CH$_3$ | H | O—CH$_3$ | 8.20 (m, 1H), 7.57 (m, 1H), 7.38 (m, 1H), 5.46 (s, 2H), 4.74 (s, 1H), 4.49 (s, 2H), 3.55 (s, 3H), 2.87 (s, 3H), 1.91 (s, 3H) |
| 15 | OCH$_3$ | CH$_3$ | H | O—THP | 8.22 (m, 1H), 7.57 (m, 1H), 7.33 (m, 1H), 5.00 (dd, 2H), 4.67 (m, 2H), 4.55 (s, 2H), 3.76 (m, 1H), 3.55 (s, 3H), 3.46 (m, 1H), 2.86 (s, 3H), 1.65-1.35 (m, 6H) |
| 16 | OCH$_3$ | CH$_3$ | H | O—CH$_2$—DMP | 8.14 (m, 1H), 7.49 (m, 1H), 7.25 (m, 1H), 7.11 (m, 1H), 6.46 (m, 1H), 6.43 (M, 1H), 4.92 (s, 2H), 4.67 (s, 1H), 4.49 (s, 2H), 4.47 (S, 2H), 3.77 (s, 3H), 3.72 (s, 3H), 3.55 (s, 3H), 2.82 (s, 3H) |
| 17 | OCH$_3$ | CH$_3$ | C$_2$H$_5$ | O—CO—OCH$_3$ | 8.17 (m, 1H), 7.51 (m, 1H), 7.35 (m, 1H), 7.03 (m, 1H), 4.71 (s, 1H), 4.58 (dd, 2H), 3.66 (s, 3H), 3.57 (s, 3H), 2.82 (s, 3H), 1.8 m (m, 1H), 1.01 (t, 3H) |
| 18 | OCH$_3$ | CH$_3$ | C$_2$H$_5$ | O—CO—CH$_3$ | 8.16 (m, 1H), 7.51 (m, 1H), 7.36 (m, 1H), 7.15 (m, 1H), 4.67 (s, 1H), 4.59 (dd, 2H), 3.56 (s, 3H), 2.83 (s, 3H), 1.82 (m, 4H), 0.98 (t, 3H) |
| 19* | OCH$_3$ | CH$_2$CHF$_2$ | H | O—CO—CH$_3$ | 8.21 (m, 1H), 7.57 (dd, 1H), 7.38 (d, 1H), 6.07 (tm, 1H), 5.44 (s, 2H), 4.81 (s, 1H), 4.59 (s, 2H), 3.76 (tm, 2H), 3.53 (s, 3H), 2.01 (s, 3H) |

*(E)-isomer; purification by means of preparative HPLC (RP18 column; eluent: acetonitrile/water gradient);

$^a$CD$_3$CN; Cypr = cyclopropyl, THP = tetrahydropyran-2-yl, DMP = 2,4-dimethoxy-phenyl Preparation of Starting Compounds
Compounds of the Formula (IV)

IV-1 iso-Propyl 4-acetoxybut-2-ynecarboxylate (cf. also analogous synthesis: R. Tayama, R. Hashimoto *Tetrahedron Lett.* 48, 7950-7952, 2007)

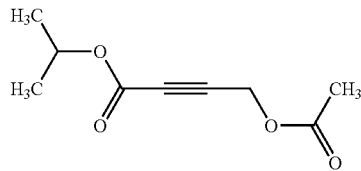

To an initial charge of 2.45 g (25 mmol) of prop-2-yn-1-yl acetate in 250 ml of anhydrous tetrahydrofuran (THF) are added dropwise, at −75° C., 27.5 ml (27.5 mmol) of a 1 M lithium bis-(trimethylsilyl)amide solution in THF. After stirring at −75° C. for 30 min, 3.68 g (30 mmol) of iso-propyl chloroformate are slowly added dropwise at −75° C. After stirring at −75° C. for 30 min, the reaction mixture is warmed to room temperature within 1 h. It is partitioned between water and dichloromethane, and the organic phase is washed successively with dilute aqueous sulphuric acid and sodium hydrogencarbonate solution. After drying over magnesium sulphate and concentrating the organic phase under reduced pressure, the residue is distilled. This gives 160 mg (3.5% of theory) of iso-propyl 4-acetoxybut-2-ynecarboxylate.

$^1$H NMR (CD$_3$CN, δ, ppm)=4.88 (sept., 1H), 4.61 (s, 2H), 1.91 (s, 3H), 1.10 (d, 6H).

IV-2

Methyl 4-acetoxyhex-2-ynecarboxylate

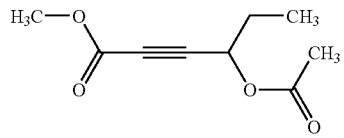

A solution of 355 mg (2.5 mmol) of methyl 4-hydroxyhex-2-ynecarboxylate (cf. J. Kunes et al., *Coll. Czech. Chem. Comm.* 66, 1809-1830, 2001) and 243 µl (3 mmol) of pyridine in 25 ml of dichloromethane is slowly admixed at 0° C. with 196 µl (3 mmol) of acetyl chloride. After 16 h at room temperature, the mixture is washed successively with dilute aqueous sulphuric acid and sodium hydrogencarbonate solution. Drying over magnesium sulphate and concentrating the organic phase affords 410 mg (89% of theory) of methyl 4-acetoxyhex-2-ynecarboxylate.

$^1$H NMR (CD$_3$CN, δ, ppm)=5.27 (t, 1H), 3.77 (s, 3H), 3.75 (s, 3H), 1.88 (m, 2H), 1.01 (t, 3H), Table 2 below lists further compounds of the general formula (IV).

TABLE 2

Compounds of the formula (IV)

$$\underset{B}{\overset{O}{\|}}C-\equiv-\underset{R^3}{\overset{D}{C}}$$

| Ex. No. | B | $R^3$ | D | Physical data: $^1$H NMR, δ [ppm]$^a$/known literature |
|---|---|---|---|---|
| IV-3 | OCH$_3$ | H | O—CO—CH(CH$_3$)$_2$ | 4.64 (s, 2H), 3.59 (s, 3H), 2.44 (sept., 1H), 0.99 (d, 6H) |
| IV-4 | OCH$_3$ | H | O—CO-Cypr | 4.64 (s, 2H), 3.58 (s, 3H), 1.48 (m, 1H), 0.78 (m, 4H) |
| IV-5 | OCH$_2$CH$_3$ | H | O—CO—CH$_3$ | 4.78 (s, 2H), 4.22 (s, 2H), 2.06 (s, 3H), 1.27 (t, 3H) |
| IV-6 | OCH$_2$CH(CH$_3$)$_2$ | H | O—CH$_3$ | 4.62 (s, 2H), 3.79 (d, 2H), 1.88 (s, 3H), 1.76 (m, 1H), 0.78 (d, 6H) |
| IV-7 | OCH$_3$ | H | O—CO—CH$_2$CH$_3$ | 4.64 (s, 2H), 3.59 (s, 3H), 2.21 (q, 2H), 0.95 (t, 3H) |
| IV-8 | OCH$_3$ | H | O—CH$_2$—DMP | 7.22 (m, 1H), 6.53 (m, 2H), 4.50 (s, 2H), 4.27 (s, 2H), 3.81 (s, 3H), 3.78 (s, 3H), 3.74 (s, 3H) |
| IV-9 | OCH$_3$ | CH$_2$CH$_3$ | O—CH$_2$—DMP | 5.27 (t, 1H), 3.77 (s, 3H), 3.75 (s, 3H), 1.88 (m, 2H), 1.01 (t, 3H) |

$^a$CD$_3$CN; Cypr = cyclopropyl; DMP = 2,4-dimethoxyphenyl

Compounds of the Formula (V)

V-1

N-[(6-Chloropyridin-3-yl)methyl]-2,2-difluoroethan-1-amine

At 45° C., 41.57 g (256.6 mmol) of 2-chloro-5-chloromethylpyridine, 20.80 g (256.6 mmol) of 2,2-difluoroethan-1-amine and 35.8 ml (256.6 mmol) of triethylamine are stirred in 500 ml of acetonitrile for 21 hours. After concentrating the reaction mixture under reduced pressure, it is taken up with 1 N aqueous hydrochloric acid and washed with ethyl acetate. The aqueous phase is alkalized with 2.5 N aqueous sodium hydroxide solution and extracted repeatedly with ethyl acetate. Concentrating the organic phase under reduced pressure affords 28.6 g (53% of theory) of N-[(6-chloropyridin-3-yl)methyl]-2,2-difluoroethan-1-amine.

$^1$H NMR (CD$_3$CN, δ, ppm)=2.93 (td, 2H), 3.80 (s, 2H), 5.85 (tt, 1H), 7.33 (d, 1H), 7.71 (dd, 1H), 8.30 (d, 1H).

In an Analogous Manner, it is Possible to Prepare:

V-2

N-[(6-Chloropyridin-3-yl)methyl]-3-fluoropropan-1-amine

LC-MS (m/z, %)=203 (MH$^+$, 100).

V-3

N-[(6-Chloropyridin-3-yl)methyl]-2-chloro-2-fluoro-ethan-1-amine

LC-MS (m/z, %)=223 (MH$^+$, 100).

Biological Examples

Example A

Lucilia Cuprina Test (LUCICU)

Solvent: dimethyl sulphoxide

To prepare an active ingredient formulation, 10 mg of active ingredient are mixed with 0.5 ml of dimethyl sulphoxide and the concentrate is diluted to the desired concentration with water. Vessels containing horsemeat, which has been treated with the active ingredient formulation of the desired concentration, are populated with Lucilia cuprina larvae.

After 2 days, the kill in % is determined. 100% means that all larvae have been killed; 0% means that no larvae have been killed.

In this test, the following compounds show an efficacy of 100% at an application rate of 100 ppm:

Ex. No.: 6, 10, 14

Example B

Myzus Test (MYZUPE Spray Treatment)

Solvent: 78 parts by weight of acetone and 1.5 parts by weight of dimethylformamide
Emulsifier: 0.5 part by weight of alkylaryl polyglycol ether To prepare an active ingredient formulation, 1 part by weight of active ingredient is mixed with the specified amounts of solvent and emulsifier, and the concentrate is diluted to the desired concentration with emulsifier-containing water.

Discs of Chinese cabbage (*Brassica pekinensis*) infested with all stages of the green peach aphid (*Myzus persicae*) are sprayed with an active ingredient formulation of the desired concentration.

After the desired time, the efficacy in % is determined. 100% means that all aphids have been killed; 0% means that no aphids have been killed.

After 5 days and at an application rate of 500 g/ha, the following compounds exhibit the efficacy specified:

Compound 1 exhibits an efficacy of 80%; compounds 8 and 14 exhibit an efficacy of 90% at an application rate of 500 g/ha; compounds 2, 3, 5, 6, 7, 9, 10, 11, 12 and 13 exhibit an efficacy of 100%.

After 6 days and at an application rate of 500 g/ha, compound 19 exhibits an efficacy of 100%.

Example C

Meloidogyne Incognita Test (MELGIN)

Solvent: 78.0 parts by weight of acetone and 1.5 parts by weight of dimethylformamide
Emulsifier: 0.5 part by weight of alkylaryl polyglycol ether To prepare an active ingredient formulation, 1 part by weight of active ingredient is mixed with the specified amounts of solvent and emulsifier, and the concentrate is diluted to the desired concentration with water. Containers are filled with sand, active ingredient solution, *Meloidogyne incognita* egg/larvae suspension and lettuce seeds. The lettuce seeds germinate and the plants develop. On the roots, galls develop. After 14 days, the nematicidal efficacy is determined by the gall formation in %. 100% means that no galls were found; 0% means that the number of galls on the treated plants corresponds to that of the untreated controls.

In this test, compound 10 exhibits an efficacy of 90% at an application rate of 20 ppm.

The invention claimed is:
1. A compound of formula (I)

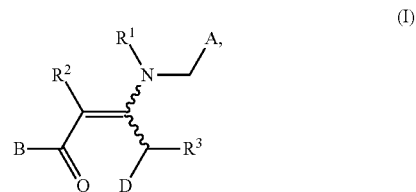

or a salt thereof,
wherein
A is a substituted heterocycle of the following formula

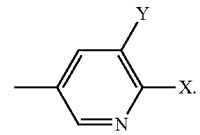

wherein
X is halogen, $C_1$-$C_6$-alkyl or halo-$C_1$-$C_6$-alkyl, and
Y is halogen, $C_1$-$C_6$-alkyl, halo-$C_1$-$C_6$-alkoxy, azido or cyano; or
A is pyrid-2-yl; pyrid-4-yl; or pyrid-3-yl which is optionally 6-substituted by fluorine, chlorine, bromine, iodine, methyl, difluoromethyl, trifluoromethyl or trifluoromethoxy; pyridazin-3-yl which is optionally 6-substituted by chlorine or methyl; pyrazin-3-yl; 2-chloropyrazin-5-yl; 1,3-thiazol-5-yl which is optionally 2-substituted by chlorine or methyl; tetrahydrofuryl; pyrimidinyl; pyrazolyl; thiophenyl; oxazolyl; isoxazolyl; 1,2,4-oxadiazolyl; isothiazolyl; 1,2,4-triazolyl; 1,2,5-thiadiazolyl which is optionally substituted by fluorine, chlorine, bromine, cyano, nitro, or is substituted by in each case optionally fluoro- and/or chlorine-substituted $C_1$-$C_4$-alkyl, $C_1$-$C_3$-alkylthio, or $C_1$-$C_3$-alkylsulphonyl;
B is a Z—$R^4$ radical in which
Z is oxygen or sulphur, and
$R^4$ is hydrogen, $C_1$-$C_6$-alkyl, $C_1$-$C_4$-alkoxy-$C_1$-$C_6$-alkyl, $C_1$-$C_4$-alkylthio -$C_1$-$C_6$-alkyl, halo-$C_1$-$C_6$-alkyl, cyano-$C_1$-$C_4$-alkyl, $C_2$-$C_6$-alkenyl, $C_2$-$C_6$-alkynyl, $C_3$-$C_6$-cycloalkyl, di-$C_3$-$C_6$-cycloalkyl-$C_1$-$C_2$-alkyl, tri-$C_1$-$C_6$-alkylsilyl, tri-$C_1$-$C_6$-alkylsilyl-$C_1$-$C_2$-alkyl, hetaryl, hetaryl-$C_1$-$C_2$-alkyl, aryl-$C_1$-$C_2$-alkyl, aryl-$C_1$-$C_2$-alkyloxy-$C_1$-$C_3$-alkyl, phenyl or a nitro-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted phenyl;
D is a T-$R^5$ radical in which
T is oxygen and
$R^5$ is hydrogen, formyl, $C_1$-$C_6$-alkyl, $C_1$-$C_4$-alkoxy-$C_1$-$C_6$-alkyl, halo-$C_1$-$C_4$-alkoxy-$C_1$-$C_6$-alkyl, $C_1$-$C_4$-alkoxy-$C_1$-$C_4$-alkoxy-$C_1$-$C_6$-alkyl, $C_1$-$C_4$-alkylthio-$C_1$-$C_6$-alkyl, $C_2$-$C_6$-alkenyl, $C_3$-$C_6$-cycloalkyl, $C_2$-$C_6$-alkynyl, $C_1$-$C_6$-alkoxycarbonyl, $C_3$-$C_6$-cycloalkyloxycarbonyl, optionally substituted aryl, tetrahydropyran-2-yl, 3-bromotetrahydropyran-2-yl, tetrahydrothiopyran-2-yl, 1,4-dioxan-2-yl, tetrahydrofuranyl, $C_1$-$C_6$-alkylcarbonyl, optionally substituted aryl-$C_1$-$C_2$-alkyl, hetaryl-$C_1$-$C_2$-alkyl, halo-$C_1$-$C_6$-alkylcarbonyl, optionally substituted arylcarbonyl, $C_1$-$C_6$-alkylsulphonyl, halo-$C_1$-$C_6$alkylsulphonyl, optionally substituted aryl-$C_1$-$C_4$-alkyloxy-$C_1$-$C_4$-alkyl, optionally substituted aryloxy-$C_1$-$C_4$-alkyl, optionally substituted arylsulphonyl or tri-$C_1$-$C_6$-alkylsilyl;

$R^1$ is hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl, $C_1$-$C_6$-alkoxy, aryl-$C_1$-$C_4$-alkyl or fluoro-substituted $C_1$-$C_6$-alkyl, $C_2$-$C_6$-alkenyl, $C_3$-$C_6$-cycloalkyl or $C_3$-$C_6$-cycloalkyl-$C_1$-$C_4$-alkyl;

$R^2$ is hydrogen, fluorine or chlorine; and $R^3$ is hydrogen or $C_1$-$C_6$-alkyl.

2. A compound according to claim 1, wherein

B is a Z—$R^4$ radical in which

Z is oxygen, and $R^4$ is hydrogen, $C_1$-$C_6$-alkyl, halo-$C_1$-$C_6$-alkyl, cyano-$C_1$-$C_4$-alkyl, $C_3$-$C_6$-cycloalkyl, di-$C_3$-$C_6$-cycloalkyl-$C_1$-$C_2$-alkyl, tri-$C_1$-$C_6$-alkylsilyl, tri-$C_1$-$C_6$-alkylsilyl-$C_1$-$C_2$-alkyl, hetaryl, phenyl-$C_1$-$C_2$-alkyl, phenyl-$C_1$-$C_2$-alkyloxy-$C_1$-$C_3$-alkyl, phenyl or a nitro-, halogen-, $C_1$-$C_4$-alkoxy-, $C_1$-$C_4$-alkylthio-, $C_1$-$C_4$-alkylsulphinyl- or $C_1$-$C_4$-alkylsulphonyl -substituted phenyl;

D is a T-$R^5$ radical in which

T is oxygen, and $R^5$ is hydrogen, formyl, $C_1$-$C_6$-alkyl, $C_1$-$C_4$-alkoxy-$C_1$-$C_6$-alkyl, halo-$C_1$-$C_4$-alkoxy-$C_1$-$C_6$-alkyl, $C_1$-$C_4$-alkoxy-$C_1$-$C_4$-alkoxy-$C_1$-$C_6$-alkyl, $C_1$-$C_4$-alkylthio-$C_1$-$C_6$-alkyl, $C_2$-$C_6$-alkenyl, $C_3$-$C_6$-cycloalkyl, $C_2$-$C_6$-alkynyl, $C_1$-$C_6$-alkoxycarbonyl, $C_3$-$C_6$-cycloalkyloxycarbonyl, optionally substituted phenyl, tetrahydropyran-2-yl, 3-bromotetrahydropyran-2-yl, tetrahydrothiopyran-2-yl, 1,4-dioxan-2-yl, tetrahydrofuranyl, $C_1$-$C_6$-alkylcarbonyl, optionally substituted phenyl-$C_1$-$C_2$-alkyl, hetaryl-$C_1$-$C_2$-alkyl, halo -$C_1$-$C_6$-alkylcarbonyl, optionally substituted phenylcarbonyl, $C_1$-$C_6$-alkylsulphonyl, halo-$C_1$-$C_6$-alkylsulphonyl, optionally substituted phenyl-$C_1$-$C_4$-alkyloxy-$C_1$-$C_4$-alkyl, optionally substituted phenyloxy-$C_1$-$C_4$-alkyl, optionally substituted phenylsulphonyl or tri-$C_1$-$C_6$-alkylsilyl;

$R^1$ is $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl, $C_1$-$C_6$-alkoxy or fluoro-substituted $C_1$-$C_6$-alkyl, $C_2$-$C_6$-alkenyl, $C_3$-$C_6$-cycloalkyl or $C_3$-$C_6$-cycloalkyl-$C_1$-$C_4$-alkyl;

$R^2$ is hydrogen, fluorine or chlorine; and $R^3$ is hydrogen or $C_1$-$C_4$-alkyl.

3. A compound according to claim 1, wherein

B is a Z—$R^4$ radical in which

Z is oxygen and $R^4$ is hydrogen, methyl, ethyl, n-propyl, iso-propyl, n-butyl, iso-butyl, sec-butyl, tert-butyl, methoxyethyl, methylthiomethyl, 2-methylthioethyl, 2,2,2-trichloroethyl, 2-chloroethyl, 2-bromoethyl, 2-iodoethyl, 2-cyanoethyl, allyl, methallyl, 3-buten-1-yl, propargyl, cyclopentyl, cyclohexyl, dicyclopropylmethyl, trimethylsilyl, di-tert-butylmethylsilyl, isopropyldimethylsilyl, trimethylsilylmethyl, 2-(2'-pyridyl)ethyl, 4-picolyl, benzyl, 4-methoxybenzyl, 2,4-dimethoxybenzyl, 4-bromobenzyl, 4-methylsulphinylbenzyl, 4-nitrobenzyl, benzyloxymethyl, 4-methylthiophenyl, 4-nitrophenyl or 2,3,4,5,6-pentafluorophenyl;

D is a T-$R^5$ radical in which

T is oxygen and $R^5$ is hydrogen, formyl, methyl, ethyl, n-propyl, iso-propyl, n-butyl, iso-butyl, sec-butyl, tert-butyl, allyl, methoxymethyl, 1-ethoxyethyl, tert-butoxymethyl, methylthiomethyl, methoxyethoxymethyl, 1-(2-chloroethoxy)ethyl, 1-methyl-1-methoxyethyl, cyclopropyl, cyclobutyl, propargyl, methoxycarbonyl, ethoxycarbonyl, cyclopropyloxycarbonyl, phenyl, tetrahydropyran-2-yl, methylcarbonyl, ethylcarbonyl, n-propylcarbonyl, iso-propylcarbonyl, tert-butylcarbonyl, trifluoromethylcarbonyl, 4-nitrophenylcarbonyl, 2,4-dinitrophenyl, 4-nitrophenyl, benzyl, 4-methoxybenzyl, 2,4-dimethoxybenzyl, 3,4-dimethoxy-benzyl, 4-nitrobenzyl, 2,6-dichlorobenzyl, 4-methoxybenzyloxymethyl, 4-nitro-benzyloxymethyl, 2-picolyl, 4-picolyl, methylsulphonyl, ethylsulphonyl, 4-methoxyphenyl, trifluoromethylsulphonyl, para-toluenesulphonyl, trimethylsilyl, triethylsilyl, triisopropylsilyl, dimethylisopropylsilyl or tert-butyldimethylsilyl;

$R^1$ is methyl, ethyl, allyl, propargyl, 2-fluoroethyl, 2,2-difluoroethyl, cyclopropyl, 2-fluorocyclopropyl or methoxy;

$R^2$ is hydrogen; and $R^3$ is hydrogen or methyl.

4. A compound according to claim 1, wherein

B is a Z—$R^4$ radical in which

Z is oxygen and $R^4$ is hydrogen, methyl, ethyl, n-propyl, iso-propyl, n-butyl, iso-butyl, sec-butyl, tert-butyl, methoxyethyl, methylthiomethyl, 2-methylthioethyl, 2,2,2-trichloroethyl, 2-chloroethyl, 2-bromoethyl, 2-iodoethyl, 2-cyanoethyl, allyl, methallyl, 3-buten-1-yl, propargyl, cyclopentyl, cyclohexyl, dicyclopropylmethyl, trimethylsilyl, di-tert-butylmethylsilyl, isopropyldimethylsilyl, trimethylsilylmethyl, 2-(2'-pyridyl)ethyl, 4-picolyl, benzyl, 4-methoxybenzyl, 2,4-dimethoxybenzyl, 4-bromobenzyl, 4-methylsulphinylbenzyl, 4-nitrobenzyl, benzyloxymethyl, 4-methylthiophenyl, 4-nitrophenyl or 2,3,4,5,6-pentafluorophenyl;

D is a T-$R^5$ radical in which

T is oxygen and $R^5$ is methylcarbonyl, ethylcarbonyl, tert-butylcarbonyl or methoxycarbonyl;

$R^1$ is methyl, 2,2-difluoroethyl or cyclopropyl;

$R^2$ is hydrogen; and $R^3$ is hydrogen.

5. A compound according to claim 1, wherein

A is pyrid-3-yl which is 6-substituted by fluorine; chlorine, bromine, methyl, trifluoromethyl or trifluoromethoxy; or is selected from 5,6-dibromopyrid-3-yl, 6-bromo-5-chloropyrid-3-yl, 6-bromo-5-fluoropyrid-3-yl, 5-chloro-6-iodopyrid-3-yl, 5,6-dichloropyrid-3-yl, 6-chloro-5-fluoropyrid-3-yl, 5-bromo-6-chloropyrid-3-yl, 6-chloro-5-methylpyrid-3-yl, 6-chloro-5-difluoromethylpyrid-3-yl, 6-chloro-1,4-pyridazin-3-yl, 2-chloropyrimid-5-yl, 2-chloro-1,3-thiazol-5-yl, 6-trifluoromethoxypyrid-3-yl, 6-chloro-1,4-pyridazin-3-yl, 6-methyl-1,4-pyridazin-3-yl, 2-chloro-1,3-thiazol-5-yl, 2-methyl-1,3-thiazol-5-yl, 2-chloropyrazin-5-yl or 2-chloro-1,3-thiazol-5-yl.

6. A compound according to claim 1, wherein
A is 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl.

7. A compound according to claim 1, wherein
A is 6-fluoropyrid-3-yl, 6-chloropyrid-3-yl, 6-bromopyrid-3-yl, 6-chloro-1,4-pyridazin-3-yl or 2-chloro-1,3-thiazol-5-yl.

8. A compound according to claim 1, wherein
A is 6-chloropyrid-3-yl, 6-bromopyrid-3-yl, or 6-chloro-1,4-pyridazin-3-yl;
B is $OCH_3$, $OCH_2CH_3$, or $OCH(CH_3)_2$;
D is a T-$R^5$ radical in which
  T is oxygen and
  $R^5$ is methylcarbonyl, ethylcarbonyl, tert-butylcarbonyl or methoxycarbonyl;
$R^1$ is methyl, cyclopropyl or 2,2-difluoroethyl; and
$R^2$ and $R^3$ are each hydrogen.

9. A compound according to claim 8, wherein A is 6-chloropyrid-3-yl.

10. A compound according to claim 9, wherein B is $OCH_3$ or $OCH(CH_3)_2$.

11. A compound according to claim 8, wherein B is $OCH(CH_3)_2$.

12. A compound according to claim 8, wherein B is $OCH_3$; and $R^1$ is methyl or 2,2-difluoroethyl.

13. A compound according to claim 8, wherein $R^5$ is methylcarbonyl.

14. A compound according to claim 7, wherein A is 6-chloropyrid-3-yl; B is $OCH(CH_3)_2$; and $R^3$ is hydrogen.

15. A composition for controlling animal pests, comprising at least one compound according to claim 1.

16. A process for preparing a compound according to claim 1, comprising:
(a) reacting a compound of formula (II)

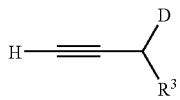

(II)

with a compound of formula (III)

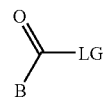

(III)

in which

B, D and $R^3$ are each as defined in claim 2; and

LG is halo-$C_1$-$C_8$-alkoxy, $C_1$-$C_8$-alkanoyloxy, mercapto, $C_1$-$C_8$-alkylthio, halo-$C_1$-$C_8$-alkylthio or halogen, optionally in the presence of a diluent and optionally in the presence of a basic auxiliary to give a compound of formula (IV); and (b) reacting the compound of formula (IV)

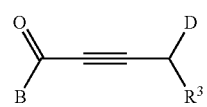

(IV)

with a compound of formula (V)

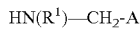

(V)

in which B, D, A and $R^1$, and $R^3$ are each as defined in claim 2, optionally in the presence of a diluent.

17. A method for controlling animal pests in an agrochemical sector, in an animal health sector or a combination thereof, comprising contacting said pests, their habitat or a combination thereof with a pest-controlling effective amount of a compound according to claim 1.

18. A method for controlling plant pests, characterized in that a compound according to claim 1 or a composition according to claim 11 is applied to the plant pests, their habitat or a combination thereof.

* * * * *